(12) United States Patent
Butenas et al.

(10) Patent No.: US 7,015,193 B2
(45) Date of Patent: Mar. 21, 2006

(54) COMPOSITIONS AND METHODS TO CONTROL BLEEDING

(75) Inventors: Saulius Butenas, South Burlington, VT (US); Kenneth G. Mann, Grand Isle, VT (US); Kathleen Brummel, Waterbury Center, VT (US)

(73) Assignee: University of Vermont, Burlington, VT (US)

( * ) Notice: Subject to any disclaimer, the term of this patent is extended or adjusted under 35 U.S.C. 154(b) by 93 days.

(21) Appl. No.: 10/125,950

(22) Filed: Apr. 19, 2002

(65) Prior Publication Data

US 2003/0050225 A1 Mar. 13, 2003

Related U.S. Application Data

(60) Provisional application No. 60/285,438, filed on Apr. 20, 2001.

(51) Int. Cl.
*A61K 38/00* (2006.01)
*A61K 35/14* (2006.01)
*A61K 35/16* (2006.01)

(52) U.S. Cl. .......................... 514/2; 514/802; 514/834; 530/380; 530/381; 530/383; 530/384

(58) Field of Classification Search ................ 514/2, 514/802, 834; 530/380, 381, 383, 384
See application file for complete search history.

(56) References Cited

U.S. PATENT DOCUMENTS 6,248,353 B1  6/2001  Singh .......................... 424/450

OTHER PUBLICATIONS

Fatouros et al. Recombinant Factor VIII SQ—Stability of VIII:C in Homogenates from Porcine, Monkey, Human Subcutaneous Tissue (Jul. 2000) J. Pharm. Pharmacol. vol. 52, pp. 797-805.*
Lawson et al. Cooperative Activation of Human Factor IX by the Human Extrinsic Pathway of Blood Coagulation (1991) J. Biol. Chem. vol. 266, No. 17, pp. 11317-1327.*
Monroe et al. Mechanism of Action of High-Dose Factor VIIa, Points of Agreement and Disagreement (2003) Arterioscler. Thromb. Vasc. Biol. vol. 23, pp. 8-9.*
Butenas et al. Influence of Factor VIIa and Phospholipids on Coagulation in "Acquired" Hemophilia (2003) vol. 23, pp. 123-129.*
Lawson et al. The Activation of Factor IX by the Tissue Factor/Factor VIIa and Factor Xa/PCPS Enzyme Complexes in a Completely Human System. (1990) Circulation, vol. 82, No. 4, Suppl. III, pp. 304, abstract 1207.*
S. Raut et al., *Brit. J. Haem.*, 107:323-329 (1999).
P. Lollar et al., *Blood*, 63(6):1303-1308 (1984).
A. R. Giles et al., *Blood*, 59(2):401-407 (1982).
J. M. Beals et al., *Biochem, J*. 235:861-869 (1986).
D. L. Higgins et al., *The Journal of Biological Chemistry*; 258(10):6503-6508 (1983).

* cited by examiner

*Primary Examiner*—David J. Steadman
*Assistant Examiner*—Holly Schnizer
(74) *Attorney, Agent, or Firm*—Edwards Angell Palmer & Dodge LLP; Robert L. Buchanan; David G. Conlin

(57) ABSTRACT

Disclosed are compositions for treating blood coagulation disorders and allows for manipulation of the blood coagulation cascade. More particularly the invention, relates to compositions for altering bleeding that include a mixture of at least one blood coagulation factor in a low dose and phospholipid vesicles. The invention has a variety of important uses including controlling bleeding in a mammal that has or is suspected of having a potentially life-threatening blood coagulation disorder.

25 Claims, 23 Drawing Sheets

COMPOSITIONS AND METHODS TO CONTROL BLEEDING

This application claims priority to U.S. Provisional Application Ser. No. 60/285,438, filed Apr. 20, 2001, the entirety of which is incorporated by reference herein.

FIELD OF THE INVENTION

The present invention generally relates to manipulation of blood coagulation. More particularly the invention relates to compositions for altering bleeding that include at least one blood coagulation factor and phospholipid vesicles. The invention has a variety of important uses including controlling bleeding in a mammal that has or is suspected of having a potentially life-threatening blood coagulation disorder.

BACKGROUND OF THE INVENTION

The blood coagulation cascade has received much attention. See generally C. van't Veer and K. Mann, *Semin. Thromb. Hemo.*, 26(4): 367–372, (2000).

More particularly, the blood coagulation cascade is thought to be initiated when subendothelial tissue factor is exposed to blood flow following either the damage or activation of the endothelium. Blood vessel damage exposes blood to cells that contain a significant amount of a transmembrane protein called tissue factor (TF). Such exposure facilitates fibrin clot formation. See e.g., C. van't Veer and K. Mann, *Semin. Thromb. Hemo.*, 26(4): 367–372, (2000).

TF is understood to be a cell surface receptor for plasma-derived coagulation factor VIIa. Binding of the serine protease factor VIIa to TF has been reported to cause a rise in catalytic efficiency of the enzyme leading to the initiation of the coagulation cascade by the activation of factors IX and X. TF is thought to be a prerequisite for the enzymatic action of factor VIIa. TF is thus an important component of normal blood coagulation.

TF forms a complex with Factor VIIa. That complex is believed to activate a fraction of the circulating zymogen factors X and IX to their respective active forms, factors Xa and IXa.

In particular, factor IXa assembles with factor VIIIa on a phospholipid surface to form an what is known as an intrinsic tenase complex. That complex is thought to produce additional factor Xa. The resulting factor Xa produced via both pathways assembles on an anionic cellular surface with factor Va into what is referred to as a prothrombinase complex. That complex activates prothrombin to α-thrombin; an important step in blood clot formation.

There is almost universal recognition that thrombin is important for the formation of a stable fibrin clot.

For example, thrombin cleaves fibrinogen and the resultant fibrin polymerizes to form the clot. Thrombin also accelerates its own generation by activation of the procofactors V and VIII and by activation of blood platelets. The activated platelets expose the necessary phospholipid equivalent surface for the formation of the factor IXa-factor VIIIa and factor Xa-factor Va enzyme complexes. Moreover, thrombin stabilizes the fibrin clot against proteolytic degradation by the fibrinolytic system via activation of the thrombin-activatable fibrinolysis inhibitor (TAFI) and via activation of factor XIII. See e.g., C. van't Veer and K. Mann, *Semin. Thromb. Hemo.*, 26(4): 367–372, (2000)).

There has been much interest in identifying and controlling bleeding disorders. See for example, C. van't Veer et al., *Blood*, 95(4): 1330–1335, (2000); C. van't Veer and K. Mann, *Semin. Thromb. Hemo.*, 26(4): 367–372, (2000); C. Negrier et al., *Semin. Thromb. Hemo.*, 26(4): 407–410, (2000); A. Shapiro, *Semin. Thromb. Hemo.*, 26(4): 413–419, (2000); S. Schulman, *Semin. Thromb. Hemo.*, 26(4): 421–424, (2000).

See also C. Negrier et al., *Semin. Thromb. Hemo.*, 26(4): 407–410, (2000); A. Shapiro, *Semin. Thromb. Hemo.*, 26(4): 413–419, (2000); S. Schulman, *Semin. Thromb. Hemo.*, 26(4): 421–424, (2000).

Particular attention has been focused on understanding the role of factor VII in blood coagulation.

For example, most factor VII is believed to circulate as a single chain zymogen (10 nM) and a trace (~10–100 pM) circulates in the active 2-chain form. Factor Xa, factor VIIa-TF, thrombin, factor IXa, and factor XIIa have been reported to activate factor VII. A comparison of the catalytic efficiencies of the potential physiologic factor VII activators showed that factor Xa, in association with phospholipids possesses the highest potency to activate factor VII. See e.g., C. van't Veer et al., (2000) *Blood*, 95(4): 1330–1335.

Specific examples of bleeding disorders are known including heritable forms such as hemophilia A and B. These disorders are believed to be impacted by deficiency of coagulation factors VIII and IX, respectively. Attempts to treat these blood disorders have involved "replacement therapy" i.e., administration of supplemental factor VIII or IX.

Other hemophilia treatment methods have involved therapy with recombinant factor VIIa. Such therapy has been reported to be effective indicating the potential for a strong factor VIIa-dependent enhancement of the thrombin generation process in vivo. There is recognition that at least part of the therapeutic effect may stem from overcoming the inhibitory effect of physiologic concentrations of zymogen factor VII on TF-dependent hemorrhagic control. See C. van't Veer and K. Mann, *Semin. Thromb. Hemo.*, 26(4): 367–372, (2000).

There is recognition that certain membrane settings may assist procoagulant complexes. For example, certain activated aggregated platelets are thought to provide procoagulant phospholipid-equivalent surfaces upon which the complex-dependent reactions of the blood coagulation cascade are localized. See K. Mann, *Thrombosis and Haemostasis;* 82(2):165–174, (1999).

There have been problems practicing prior therapeutic methods for treating blood coagulation disorders with blood coagulation factors such as recombinant Factor VIIa (rFVIIa).

For example, most commercial sources of Factor VIIa are expensive. Much needed treatment can involve high consumption of the blood factor. Supraphysiological levels of recombinant factor VIIa (~300 X normal) are often needed to treat hemophilia. Accordingly, prior treatment methods can be prohibitively expensive for some patients. See J. Ingerslev, *Seminars in Thrombosis and Hemostasis;* 2000, 26(4):425–432.

There have been other problems implementing prior strategies to treat blood coagulation disorders.

For example, a particular disadvantage of treatments involving recombinant FVIIa (rFVIIa) is that this factor has a short half life. Moreover, many rFVIIa treatment protocols require multiple injections (frequently>100). Many of the protocols require treatment over an extended period of time, especially after surgical procedures. Patient inconvenience and discomfort has been substantial.

There have been attempts to address these and related shortcomings, particularly with respect to treatment regimens involving rFVIIa. For example, continuous rFVIIa infusion therapies have been adopted. However, the costs of such treatment are often expensive. See S. Schulman, *Semin. Thromb. Hemo.*, 26(4): 421–424, (2000).

Recombinant factor VIIa has been extensively used for the treatment of hemophilia A and B patients with inhibitors, although the exact mechanism by which this enzyme, used at supraphysiological concentrations, restores normal hemostasis is not secure. Additionally, the lack of correlation between the in vivo factor VIIa levels during the treatment and the efficacy of the treatment, makes the outcome of treatment somewhat unpredictable. See Santagostino E, et al., Relationship between factor VII activity and clinical efficacy of recombinant factor VIIa given by continuous infusion to patients with factor VIII inhibitors. *Thromb Haemost.* 2001;86:954–958.

Other drawbacks to conventional therapies used to treat blood coagulation disorders including danger from infectious viruses including those capable of disabling the immune system (e.g., HIV). Methods have developed to ensure blood factor purity. However, complete safety has been difficult to ensure.

Another major drawback to conventional therapies used to treat blood coagulation disorders is that some patients develop high-titer, inhibitory antibodies to blood coagulation factors. Therefore, such patients can no longer be treated with conventional blood coagulation factor replacement therapy and alternative methods for treatment need to be found.

It would also be desirable to have compositions for preventing or treating blood clotting disorders that are cost effective and require relatively short treatment times for optimal results. It would be further desirable to have compositions which include at least one blood coagulation factor, preferably activated, and phospholipid to enhance function of the composition.

SUMMARY OF THE INVENTION

We have now discovered compositions and methods for treating blood coagulation disorders that decrease need for administered blood coagulation factors. Practice of the invention desirably enhances activity of the blood factors and helps minimize the cost and inconvenience of most standard therapeutic protocols used to treat unwanted bleeding. The invention has a wide spectrum of useful applications including preventing or treating a blood coagulation disorder or acute blood loss in a human patient.

More particularly, the present invention relates to compositions that include a mixture of at least one specific phospholipid and at least one serine protease-activated blood coagulation factor. Preferred blood coagulation factors according to the invention are incapable of binding Factor Va as determined e.g., standard assays that measure thrombin generation assay, specifically thrombin-antithrombin-III complex (TAT) formation. Further preferred factors suitable for use with the invention are provided as recombinant and activated preparations including, but not limited to, commercially available preparations consisting essentially of Factor VIIa. Without wishing to be bound to theory, it has been found that contact between certain phospholipid mixtures of this invention and blood coagulation factors boosts activity of the blood coagulation factor. Such enhanced activity can be detected and quantified desired by use of what is referred to herein as a synthetic "plasma" test. See for instance, the results set forth in Examples 5 and 6 which follow. Another assay used in the present invention is the whole blood coagulation test. See for instance, the results set forth in Example 7 which follows.

Accordingly, and in one aspect, the invention provides compositions for controlling bleeding in a mammal. Preferred compositions are pharmaceutically acceptable. In one embodiment, the composition includes a coagulation-effective amount of at least one type of phospholipid (preferably as a vesicle mixture) and at least one substantially pure mammalian blood coagulation factor. Illustrative compositions of the invention are provided as recombinant or natural preparations that include at least one of Factor VIIa, Factor IXa, Factor XIa, or Factor VIIIa. Mixtures of these activated factor preparations are also contemplated. More preferred compositions include Factor VIIa, preferably rFVIIa in combination with phospholipid vesicles.

Practice of the invention provides a variety of important advantages. For example, in m many embodiments, the invention requires relatively low amounts of blood coagulation factor (when compared to conventional therapies) and still provides a beneficial coagulation effect. This feature of the invention reduces the need for sometimes costly blood coagulation factors, thereby reducing the cost and efficaciousness of therapy. These and other invention advantages will make blood coagulation therapy much more affordable to hospitals and the general public.

Other Important Advantages are Provided by the Invention.

For example, in many cases it is desirable to decrease or eliminate risk of an adverse immune response against administered blood coagulation factors. That is, by administering less of the factor in accord with the invention, the risk of aggravating the immune system is lessened. This feature of the invention also decreases the chance of developing potentially life-threatening anti-blood coagulation factor antibodies. Patient health and immune tolerance is expected to be positively impacted by use of the invention.

Additionally, risk of pathogen contact is decreased by the use of recombinant proteins and/or the lower amounts of administered blood coagulation factor required by the invention.

As will become more apparent from the discussion and Examples below, the present invention is compatible with a variety of suitable phospholipid vesicles. More preferred phospholipids are capable of enhancing the activity of the blood coagulation factors as determined by the standard synthetic "plasma" test and whole blood coagulation experiments in the examples which follow. Preferred compositions of the invention will include at least two phospholipid types as vesicles and will demonstrate an increased Factor VIIa activity by at least about 10 fold, preferably 100 fold, more preferably 1000 fold as determined by the standard synthetic "plasma" test and whole blood coagulation experiments. Related compositions including one or more other blood coagulation factors will be enhanced similarly as determined by the plasma test.

Typically preferred phospholipid vesicles for use with the compositions of this invention include anionic phospholipids having a pH of between about 6 to 8, preferably about 7.2. More preferred anionic phospholipids are mixtures of phosphatidylcholine and phosphatidylserine (PCPS) provided in an amount sufficient to enhance activated blood coagulation factor activity by at least about 10 fold as determined by the standard synthetic "plasma" test and whole blood coagulation experiments. For most invention applications, that amount will be between from about 50% (w/v) to about 90% (w/v) phosphatidylcholine and from between about 10% (w/v) to about 50% (w/v) phosphatidylserine. However, other ranges of the phosphatidylcholine and the phosphatidylserine may be more suitable for other in vivo applications.

The Phospholipid Component of the Invention Provides Specific Advantages.

In particular, it helps address problems associated with many prior bleeding treatment methods. That is, and without wishing to be bound to theory, it appears that providing the phospholipids in accord with the present invention forms a surface well-suited to enhancing blood factor activity and particularly the activity of rFVIIa. Less factor is need to achieve beneficial effect. A key advantage is that the therapeutic effective dose of blood coagulation factors is drastically reduced, thereby reducing costs associated with the treatment of bleeding disorders. Patients suffering from hemorrhaging or other chronic blood loss maladies sometime associated with surgery are also expected to benefit significantly from the invention.

In another embodiment, the invention provides methods for controlling bleeding in a mammal using one blood coagulation factor and phospholipid vesicles is provided. Typically, the method comprises administering to the mammal a pharmaceutically acceptable composition comprising a coagulation-effective amount of at least one blood coagulation factor, which does not form a specific binding complex with Factor Va, and phospholipid vesicles.

More particularly, the pharmaceutically acceptable composition is administered in a coagulation-effective amount between from about 10 to about 1000 fold less then a therapeutic amount of the blood coagulation factor. Preferred administration amounts generally, but not exclusively, are in the range of between about 0.1 nM to about 10 nM.

The invention also provides methods for controlling bleeding in a mammal. In one embodiment, the method includes administering to the mammal a pharmaceutically acceptable composition that includes a recombinant Factor VIIa in an amount of from between about 0.1 nM to about 10 nM. Phospholipid vesicles according to the invention are preferably also included. More particularly, the phospholipid vesicles comprise phosphatidylcholine and phosphatidylserine (PCPS). In another embodiment, the PCPS comprise between from about 50% (w/v) to about 90% (w/v) phosphatidylcholine and between from about 10% (w/v) to about 50% (w/v) phosphatidylserine. Other suitable ranges of phospholipids are acceptable provided they enhance activity of one or more preferred blood coagulation factors by at least about 10 fold as determined by the standard synthetic plasma assay.

In another embodiment, the invention provides methods for reducing the amount of blood coagulation factor required by a mammal in need of such treatment. The method generally includes contacting the coagulation factor with phospholipid vesicles, including the PCPS already mentioned, and administering to the mammal an amount of the blood coagulation factor less than the therapeutic amount. More particularly, the preferred therapeutic amount of blood coagulation is administered in lower therapeutic effective doses as compared to the doses used in conventional therapy where the coagulation factors are usually administered as highly concentrated purified factors. More particularly, the preferred therapeutic dose administered is preferably about 10 fold less amount, more preferably the therapeutic dose is about 100 fold less, most preferably the therapeutic dose is about 1000 fold less than the therapeutic doses used in present treatments of patients suffering from hemophilia, or suffering from a life-threatening loss of blood.

Additional aspects and advantages of the invention are disclosed infra.

BRIEF DESCRIPTION OF THE DRAWINGS

FIG. 9A is a graph showing thrombin generation over time.

FIG. 9B is a graph showing maximum rates of thrombin generation.

FIG. 9C is a graph showing the duration of the initiation phase.

FIG. 10A is a graph showing the clotting time.

FIG. 10B is a graph showing thrombin generation rate dependence on PCPS concentration.

FIG. 11A is a graph showing TAT formation.

FIG. 11B is a graph showing platelet osteonectin release.

FIG. 11C is a graph showing FPA release.

DETAILED DESCRIPTION OF THE INVENTION

Figure 1:
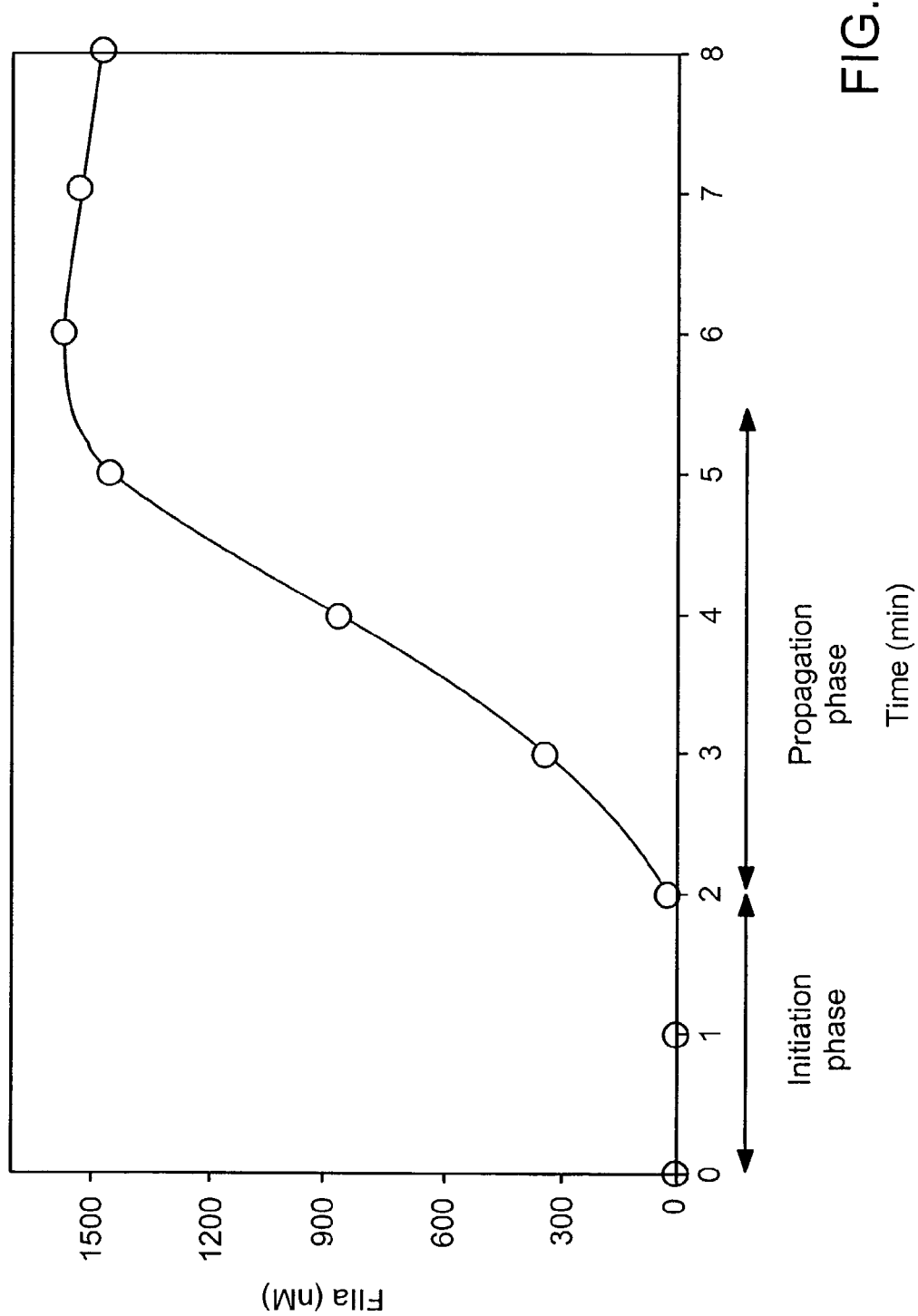
FIG. 1 is a graph showing the procoagulant process is divided into two phases: the initiation phase and the propagation phase.

As discussed, this invention relates to the therapeutic treatment of patients with bleeding disorders involving administering a mixture of phospholipids with serine protease-activated blood coagulation factors. Preferred invention compositions act synergistically to boost activity of activated blood coagulation factors, preferably FVIIa such as recombinant forms thereof typical of many commercial preparations. As also discussed, preferred practice of the invention provides substantial advantages including reducing treatment costs, decreasing factor dosages, reducing risk of an immune reaction, such as anaphylaxis, and also decreases the risk of antibody formation specific for the blood coagulation factors. Furthermore, inhibitors of blood coagulation factors are not produced, thus therapy is simplified.

Preferred therapeutic compositions of the present invention include between from about 0.1 nM to about 10 nM of activated blood coagulation factors, typically recombinant Factor VIIa (rFVIIa) and selected phospholipid vesicles. As discussed previously, particular phospholipid vesicles comprise anionic phospholipids at about physiological pH, preferably phosphatidylcholine and phosphatidylserine (PCPS). The preferred weight to volume (w/v) of PCPS, is comprised between from about 50% (w/v) to about 75% (w/v) phosphatidylcholine and between from about 10% (w/v) to about 25% (w/v) phosphatidylserine. More preferably, the weight to volume (w/v) of (PCPS), is comprised between from about 75% (w/v) to about 90% (w/v) phosphatidylcholine and between from about 25% (w/v) to about 50% (w/v) phosphatidylserine. Most preferably, the weight to volume (w/v) of (PCPS), is comprised between from about 50% (w/v) to about 90% (w/v) phosphatidylcholine and between from about 10% (w/v) to about 50% (w/v) phosphatidylserine. Preferred use of the composition involves administration of a coagulation-effective amount usually between from about 10 to about 1000 fold less the amount of the same factor used in conventional therapies.

Although it will be appreciated that precise dosage and treatment regimens will vary according to recognized parameters including, but not limited to, patient health, age, sex, etc., a preferred unit dose of the PCPS is between from about 1 arbitrary unit to about 300 arbitrary units per kg body weight, more preferably the unit dose of the PCPS is between from about 300 arbitrary units to about 1,500 arbitrary units per kg body weight of the mammal, most preferably the unit dose of the PCPS is between from about 1 arbitrary units to about 3,000 arbitrary units per kg body weight of the mammal. As used herein, 1 arbitrary unit is defined as 0.005 mg per kg body weight.

The therapeutic compositions of the present invention, more particularly include an effective mixture of PCPS and blood coagulation factor, typically recombinant factor VIIa. A preferred unit dose range of the amount of recombinant Factor VIIa is between from about 18 units to about 180 units per kg of body weight of the mammal. A more preferred unit dose range of the amount of recombinant Factor VIIa is between from about 180 units to about 900 units per kg of body weight of the mammal. A most preferred unit dose range of the amount of recombinant Factor VIIa is between from about 18 units to about less than 1,800 units per kg of body weight of the mammal.

A preferred weight ratio of the PCPS to the blood coagulation factor for most invention applications is between from about 0.15:1 to about 10,000:1. A more preferred weight ratio of the PCPS to the blood coagulation factor administered to a patient is between from about 0.15:1 to about 20,000:1. A most preferred weight ratio of the PCPS to the blood coagulation factor administered to a patient is between from about 0.15:1 to about 30,000:1.

In order to produce the desired therapeutic effect, as embodied in this invention, the composition is desirably administered by a continuous intravenous infusion, using isotonic saline for injection to keep the vein open. The treatment may consist of a single dose or a plurality of doses over a period of time. An advantageous treatment schedule requires administration of the above-described therapeutic composition with an interval between administrations calculated on a per patient basis. As already discussed briefly, factors to consider in the treatment regimen would be weight, age, bleeding disorder, severity of bleeding etc. Those who are skilled in the art may modify the regimen according to the individual patient.

"Synthetic plasma" as used herein refers to a composition of highly purified natural and recombinant proteins involved in the coagulation and its regulation and synthetic phospholipid membranes or platelets.

"Synthetic plasma test" as used herein refers to the use of synthetic plasma wherein phospholipid combinations, concentrations, blood coagulation activity of blood coagulation factors, blood coagulation effective amounts, and the like, are determined by the most optimal compositions that cause coagulation. See for example K. G. Mann, *Thrombosis and Haemostasis*, (1999), 82(2):165–174 and also Examples 5–8 described infra.

As used herein "an effective blood coagulation amount" is the minimum amount of blood coagulation factor required for blood clotting in a time less than ten minutes, as determined by the synthetic "plasma" test or blood coagulation experiments. See methods and examples 6 and 7 described infra. The preferred blood coagulation factors are Factor VIIa, Factor VIIIa, Factor IXa, Factor XIa, more preferably, recombinant Factor VIIa. An effective blood coagulation amount, for example for recombinant factor VIIa, is typically in the range between from about 0.1 nM to about 10 nM. (about 18 units per kg body weight to about 1,800 units per kg body weight).

A "pharmaceutically acceptable composition" as used herein, is a therapeutic composition of the present invention employed in a physically discrete unit suitable as unitary dosages for a primate such as a human, each unit containing a pre-determined quantity of active material calculated to produce the desired therapeutic effect in association with the required phospholipid vehicle. Precise coagulation-effective amounts of the therapeutic composition to be administered will be guided by the judgment of the practitioner, however, the unit dose will generally depend on the route of administration.

"Pharmaceutically acceptable" as used herein, refers to compositions that are not toxic to the patient and do not interfere with the desired activity of the blood coagulation factors, of the present invention.

"Substantially pure" as used herein, refers to the blood coagulation factors obtained as a result of the purification procedure described in van t' Veer et al., *J. Biol. Chem.*, (1997) 272:4367–4377, the teachings of which are specifically incorporated herein.

The term "mammal" as defined herein preferably refers to a primate such as a human being or an animal.

As used herein, the term "platelet activation" refers to platelet release reactions (e.g., osteonectin, platelet factor 4 or β thrombomodulin). However, platelet activation can also refer to the occurrence of one or more of the following events: platelet aggregation, platelet adhesion, platelet agglutination, expression of platelet external receptors (e.g., GPIIb/IIIa or P-selectin), or platelet interaction with other blood components (e.g., collagen or fibrinogen) and cells (e.g., leukocytes).

As discussed, the invention is compatible with a variety of suitable phospholipid vesicle mixtures. In particular, preferred phospholipids can be provided in a number of forms but the preferred form is as phosphatidylcholine/phosphatidylserine vesicles (PCPS). The PCPS vesicle preparations and the method of administration of Xa/PCPS is described in Giles, et al., U.S. Pat. No: 4,721,618 (1988), the teachings of which are specifically incorporated herein. For example, phospholipid vesicles or liposomal suspensions are also preferred as pharmaceutically acceptable carriers or delivery vehicles. These can be prepared according to methods known to those skilled in the art and can contain, for example, phosphatidylserine/phosphatidylcholine or other compositions of phospholipids or detergents.

Blood coagulation factors suitable for use with the invention can be prepared or purchased from commercial vendors as needed. For example, recombinant FVIIa can be purchased from Novo Biolabs (Danbury, Conn.) and is the preferred source for purposes of this invention. The amount of recombinant factor VIIa in the dosage form is extremely small and allows for treatment of large numbers of hemophiliacs, in comparison to the high doses required for the provision of more conventional therapy. This has distinct advantages, apart from the obvious one of economy. The accidental transmission of infection is a major hazard of multiple transfusion practice in patients such as hemophiliacs. Hepatitis and acquired immunodeficiency syndrome are major problems.

There are other sources available to obtain factor VII, for example it can be purified from plasma and activated into Factor VIIa by the methods described by Broze and Majerus, *J. Biol. Chem.* 255 (4) (1980) 1242–1247 and Hedner and Kisiel, *J. Clin. Invest.* 71 (1983) 1836–1841.

Factor VIIa may also be produced by recombinant DNA-technology by culturing in an appropriate medium mammalian cells transfected with a DNA-sequence encoding Factor VII, isolating the protein produced and activating said protein to Factor VIIa (European patent application No. 86302855.1).

Human coagulation factors, such as for example VII, X, IX, and prothrombin may also be isolated from fresh frozen plasma using the general methods of Bajaj et al, (*Prep. Biochem.*, 11:397–412, 1981).

FVIIa biological activity: The FVIIa biological activity is characterized by the mediation of blood coagulation via the synergistic mixture of a phospholipid and FVIIa.

Biological activity, as used herein, is a function or set of functions performed by a molecule in a biological context (i.e. in an organism or an in vitro facsimile). Biological activities of proteins may be divided into catalytic and effector activities. Catalytic activities of clotting factors generally involve the activation of other factors through the specified cleavage of precursors. Effector activities including specific binding of the biologically active molecule in a calcium-dependent manner, to macromolecules such as proteins or to cells. Effector activity frequently augments, or is essential to, catalytic activity under physiological conditions. Catalytic and effector activities may, in some cases, reside within the same domain of a protein.

The preparations according to the invention enable a safe and simple treatment of blood coagulation disorders, in which an effective onset of action can be observed within a very short time. Other conditions that can be treated with this combination include surgical bleeding from the microvasculature, bleeding at skin graft harvest sites, post-operative bleeding, including following orthopedic surgery, brain surgery or brain trauma, bleeding secondary to thrombocytopenia, and platelet dysfunction.

In a particularly preferred invention embodiment, compositions include synthetic phospholipids: 75% phosphatidylcholine and 25% phosphatidylserine, with 10 nM recombinant factor VIIa. Phosphatidylcholine (PC) and phosphatidylserine (PS) are available commercially as semi-purified reagents and are prepared from egg yolks and bovine brain respectively. The PCPS lipid vesicles may be prepared by a conventional and standardized protocol (Nesheim et al, *J. Biol. Chem.* 254: 10952, 1979 and Barenholz et al., *Biochem. J.* 16:2806, 1976) which produces single compartment vesicles of uniform dimension (325–350 Å) which may be stored at 4° C. for 2 to 3 weeks. The molar ratio of phosphatidylserine to phosphatidylcholine is about 1:3, based on the relative amounts of these lipids used in the preparation of the vesicles. The recombinant factor VIIa-PCPS mixture is freshly prepared by mixing recombinant factor VIIa and PCPS in the desired ratio immediately prior to use.

The dosage of recombinant factor VIIa/PCPS is administered on a dose/kg body weight basis. The dose of PCPS is unitized in arbitrary units. 1 Arbitrary unit PCPS equals $1 \times 10^{-8}$ moles of phospholipid as assayed by an inorganic phosphorus assay. Recombinant factor VIIa is unitized according to an internationally accepted classification in which 1 unit of factor VII is the amount present in 1 ml of normal plasma and 1 unit of factor VIIa is the amount of activity present when 1 unit of factor VII is fully activated. The assay is standardized by measuring activity in the test preparation against the activity in a normal pool plasma standard as described by Suomela H., et al (*Thrombosis Research* 10:267, 1977) as modified by Giles A. R. et al (*Thrombosis Research* 17; 353, 1980). The activity of the purchased recombinant factor VIIa (Novo Biolabs) is 50,000 units per mg.

For the methods of present invention, the preferred method for administration of the blood coagulation factors is intravenous administration. A continuous infusion is established via butterfly needle in the femoral vein using isotonic saline for injection to keep the vein open.

In the case of internal bleeding or for systemic bleeding, the composition may be suitable for enteral application. The composition may be encapsulated in an acid-stable, base-labile coating (e.g. an enteric pill which is coated with a substance such as salol which will not dissolve in the stomach or a hexylresorcinol pill which consists of hexyl-resorcinol covered with a rupture resistant coating that disintegrates in the digestive tract). The pill would be stable in the acidic stomach, but would become "activated" as it enters the high pH small intestine.

The preparations according to the invention enable a safe and simple treatment of blood coagulation disorders, in which an effective onset of action can be observed within a very short time. Other conditions that can be treated with this combination include surgical bleeding from the microvasculature, bleeding at skin graft harvest sites, post-operative bleeding, including following orthopedic surgery, brain surgery or brain trauma, bleeding secondary to thrombocytopenia, and platelet dysfunction.

It will be appreciated that the actual preferred amounts of blood coagulation factors used in a given therapy will vary according to the blood coagulation factors used or combination of blood coagulation factors being utilized, the phospholipid vesicle composition, the mode of application, the particular site of administration, etc. Optimal administration rates for a given protocol of administration can be readily ascertained by those skilled in the art.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. Various references are cited herein, the disclosure of which are incorporated by reference in their entireties.

The present invention is further illustrated by the following Examples. These Examples are provided to aid in the understanding of the invention and are not construed as a limitation thereof.

The following Materials and Methods were used as needed to conduct the Examples which follow.

Phosphatidylserine (PS), phosphatidylcholine (PC), and EDTA were purchased from Sigma. Phospholipid vesicles (PCPS) composed of 25% PS and 75% PC were prepared as described (1). Spectrozyme TH was purchased from American Diagnostica, Inc. D-Phe-Pro-ArgCH$_2$Cl(FPRck) was synthesized in home. ELISA thrombin-AT-III (TAT) kit (Enzygnost TAT) was purchased from Behring. Osteonectin ELISA plates were coated in home. Monoclonal anti-osteonectin and anti-factor IX antibodies were developed in the Biochemistry Antibody Core Laboratory (University of Vermont). Fibrinogen, fibrinopeptide A (FPA) and B (FPB), and solid clot analyses were performed as described previously (2).

*Proteins.* Human coagulation factors VII, X, IX, and prothrombin, were isolated from fresh 10 L frozen plasma using the general methods of Bajaj et al. (3), and were purged of trace contaminants and traces of active enzymes as described (4). Recombinant factor VIII and recombinant tissue factor (TF) (residues 1–242) were provided as gifts from Drs. Shu Len Liu and Roger Lundblad (Hyland division, Baxter Healthcare Corp). Recombinant human factor VIIa was purchased from NOVO Pharmaceuticals. Recombinant full-length TFPI produced in *Escherichia Coli* was purchased from American Diagnostica. Corn trypsin inhibitor was isolated from popcorn as described elsewhere (7). Washed platelets were prepared by the procedure of Mustard et al. (8). Relipidation of TF was done as described elsewhere (7).

Human factor V and AT-III were isolated from freshly frozen plasma (5, 6). Briefly, human coagulation factor VII was isolated from the factor VII containing fractions eluted in the NaCl gradient of the DEAE-Sepharose chromatography, involved in the purification of vitamin K-dependent clotting factors. Factor VII activity in the fractions was measured by incubating 25 $\mu$l of 1000-fold diluted samples in 20 nmol/L Tris, 150 nmol/L NaCl, pH 7.4 (TBS) containing 0.1% bovine serum albumin (BSA) with 50 $\mu$l of a solution containing 1/300 diluted rabbit thromboplastin (Thromboplastin-C, Dade, Baxter), 160 nmol/L factor X, and 10 nmol/L CaCl$_2$ for 30 minutes. Generation of factor Xa was monitored using the chromogenic substrate Spectrozyme Xa. Factor VII eluted from the DEAE-Sepharose before and with some overlap with the first part of the C4BP/protein S peak. C4BP/protein S-containing fractions were not included in the factor VII pool. The factor VII pool was diluted 1.5 times with water containing 1 nmol/L benzamidine and applied to a 20 ml Q-Sepharose FF column previously equilibrated in 17 nmol/L Tris, 50 mmol/L NaCl, and 1 mmol/L benzamidine, pH 7.4. After application of the pool, the column was washed with 100 ml-equilibration buffer. Factor VII activity was eluted with 20 mmol/L CaCl$_2$ in the same buffer. Fractions were collected in 1/10 of a volume of 0.4 mol/L EDTA pH 7.4. Factor VII containing fractions were pooled and precipitated by adding ammonium sulfate to 80% saturation. This solution was kept overnight at 4° C., then spun in an SW-50 Rotor at 40 000 rpm, 4° C. for 45 minutes. The protein pellet was resuspended in 50% glycerol and stored at -20° C. Before use in the experiment, factor VII was dialyzed extensively against TBS at 4° C. Factor VII prepared via this method appeared homogeneous on nonreduced and reduced SDS-Page and had a specific activity of 2000 U/mg measured in a single clotting assay.

Coagulation Factor Experiments

Thrombin generation initiated by factor VIIa-TF was studied in a reconstituted coagulation model as described previously. TF was relipidated at the indicated concentrations in 400 µmol/L 75% phosphatidylcholine, 25% phosphatidylserine vesicles for 30 minutes at 37° C. in 20 mmol/L Hepes, 150 mmol/L NaCl, 2 mmol/L CaCl$_2$ pH 7.4 (Hepes/Ca$^{2+}$). Factor V and factor VIII were added to the relipidated TF mixture immediately before the reaction was started by the addition of a solution containing factor VIIa with or without factor VII and factor X, factor IX, and prothrombin. The zymogen solution was also prepared in Hepes/Ca$^{2+}$ and preheated at 37° C. for 3 minutes before addition to the TF, factor V, and factor VIII mixture. When TFPI or AT-III were included, they were added to the factor X, factor IX, and prothrombin mixture.

The final concentrations of the proteins in the reaction, chosen to represent mean plasma values, were 160 nmol/L factor X, 90 nmol/L factor IX, 0.7 nmol/L factor VIII, 20 nmol/L factor V, 1.4 µmol/L prothrombin, 2.5 nmol/L TFPI, and 3.4 µmol/L AT-III. After starting the reaction, aliquots were withdrawn from the reaction mixture in time and quenched in 20 mmol/L EDTA/TBS pH 7.4 to assay for thrombin formation. Assays for thrombin activity were performed using the chromogenic substrate Spectrozyme TH. The hydrolysis of the substrate was monitored by the change in absorbance at 405 nm. Thrombin generation was calculated from a standard curve prepared by a serial dilution of α-thrombin. When AT-III was added to the reaction mixture, samples were withdrawn in 20 mmol/L EDTA/TBS, containing 0.4 mmol/L Spectrozyme TH, and assayed immediately for thrombin activity as described before, to obtain accurate thrombin measurements in the presence of AT-III.

EXAMPLE 1

Treatment of Hemophilia A Blood with Factor VIIa

Figure 3A:
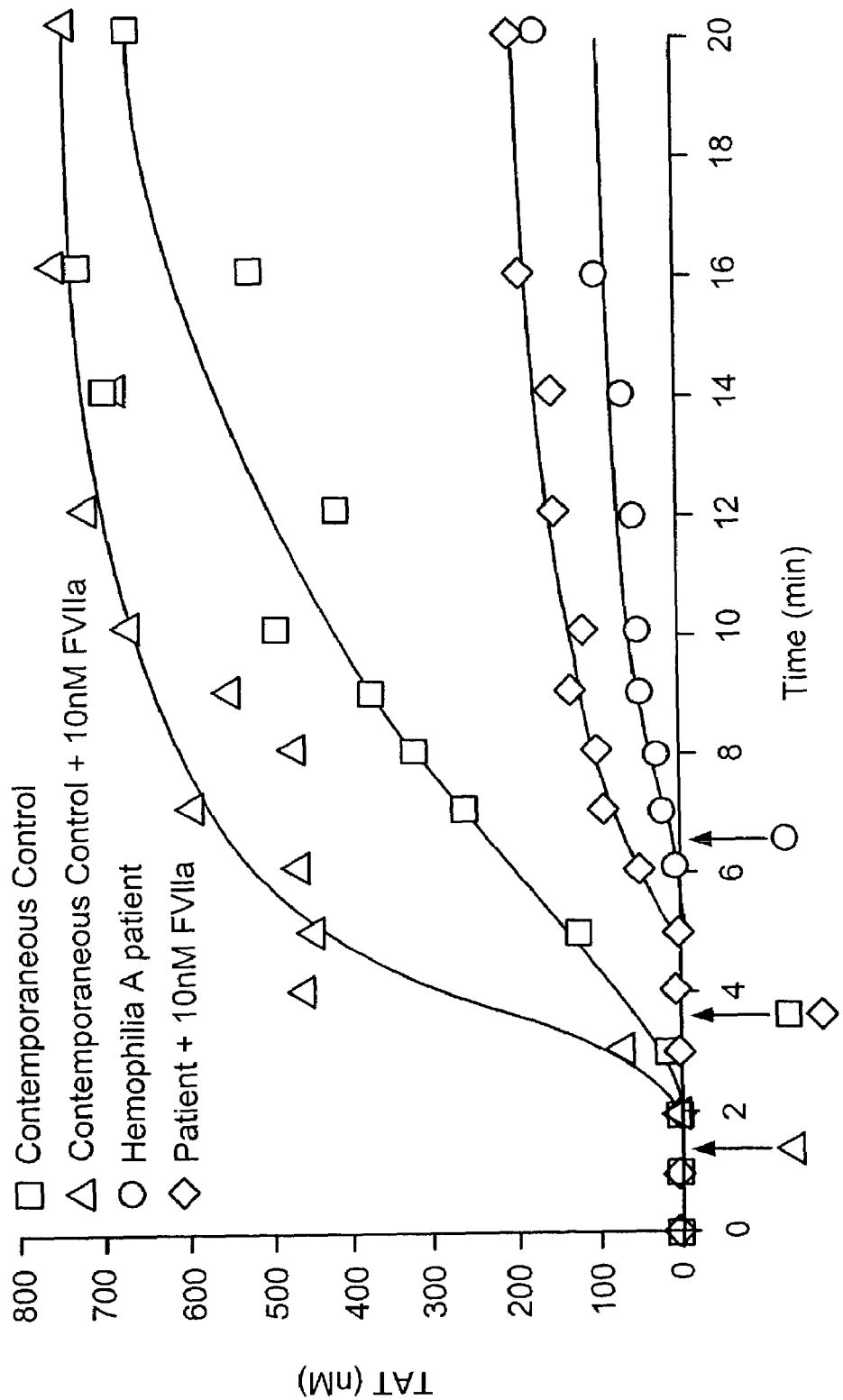
FIG. 3A is a graph which demonstrates the shortening of blood clotting time by addition of 10 nM of factor VIIa (arrows indicate clotting time). Thrombin generation is barely elevated (diamonds) by the addition of factor VIIa to hemophilia A blood as compared to blood without factor VIIa addition (circles).

Clotting in freshly drawn, non-anticoagulated whole blood was performed in 32 tubes (two series per experiment—16 tubes/series). All tubes were loaded with corn trypsin inhibitor (100 µg/ml blood), 12.5 pM relipidated TF/ml blood (PCPS:TF=2,000) in HBS with 2 mM CaCl$_2$ (all tubes in each series except phlebotomy control tube), 10 nM recombinant factor VIIa (all tubes, experiment series only), and equivalent volume factor VIIa dilution buffer (HBS, pH 7.4, all tubes control series only). No more than 35 µl of reagents were loaded in each tube. The zero tube of each series was pretreated using 1 ml of 50 mM EDTA and 10 µl of 10 mM FPRck (diluted in 0.01 M HCl). Normal donor or hemophilia A patient (factor VIII<1%) blood was drawn by venipuncture, delivered into the reagent-loaded tubes, and the tubes were periodically quenched with EDTA and FPRck. The clotting time was observed visually by two observers. Tubes were centrifuged and the supernatants were aliquoted for further analyses. ELISAs for TAT were performed. FPA and FPB release was evaluated by HPLC, fibrinogen depletion by Western blots. Solid clots were solubilized and analyzed by gel electrophoresis. The results of this experiment are shown in FIG. 3A (TAT formation), wherein (■) represents normal control; (▲) represents normal control with 10 nM factor VIIa addition; (•) represents Hemophilia A patient; and (◇) represents Hemophilia A patient with 10 nM factor VIIa addition.

Figure 3B:
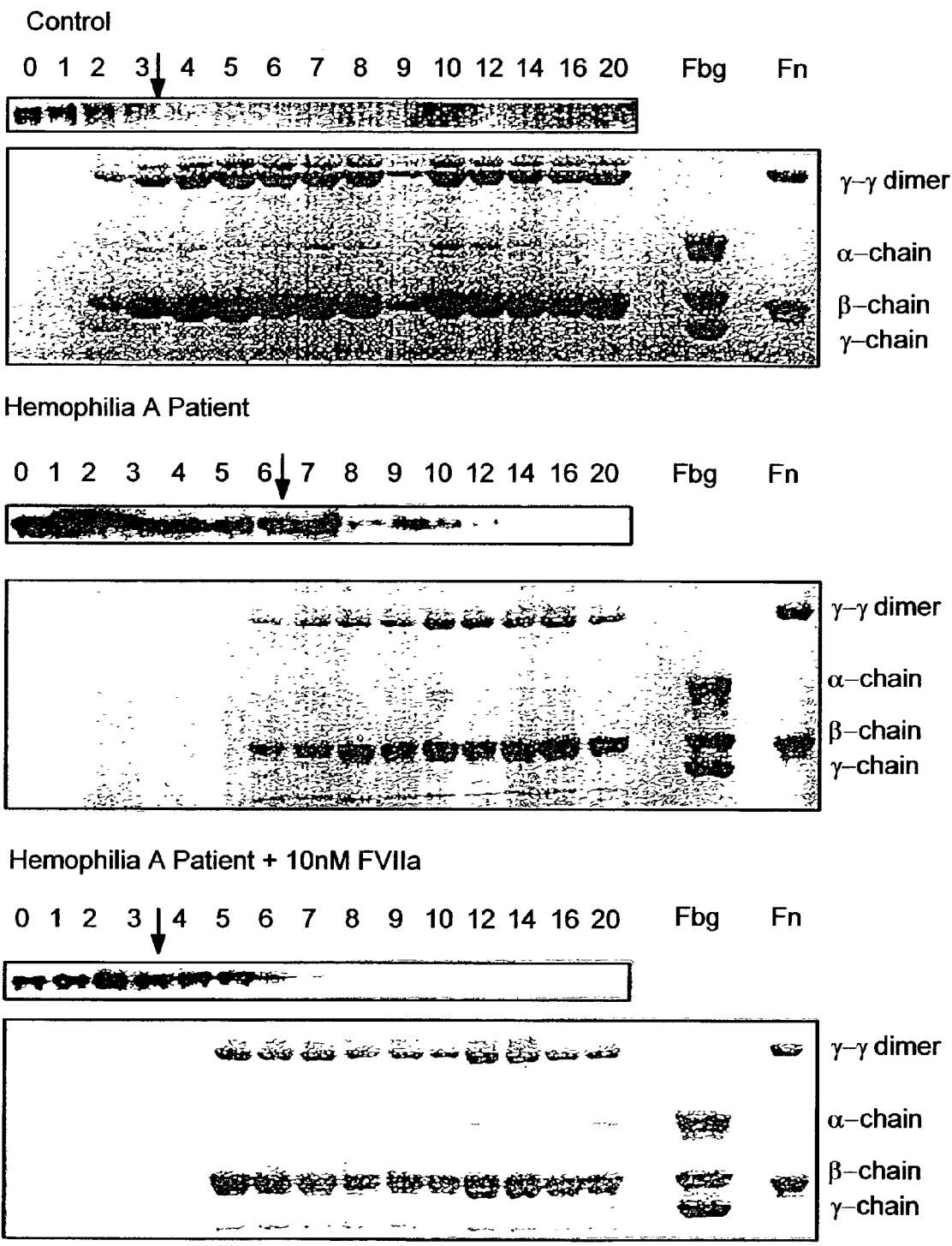
FIG. 3B is a photograph of a gel which demonstrates that addition of factor VIIa has no effect on the solid clot formation.

In FIG. 3B, the upper lanes in each panel represent gels of soluble fibrinogen, lower parts represent gels of solubilized solid clots.

EXAMPLE 2

Treatment of Induced Hemophilia B Blood with PCPS and Factor VIIa

Figure 3C:
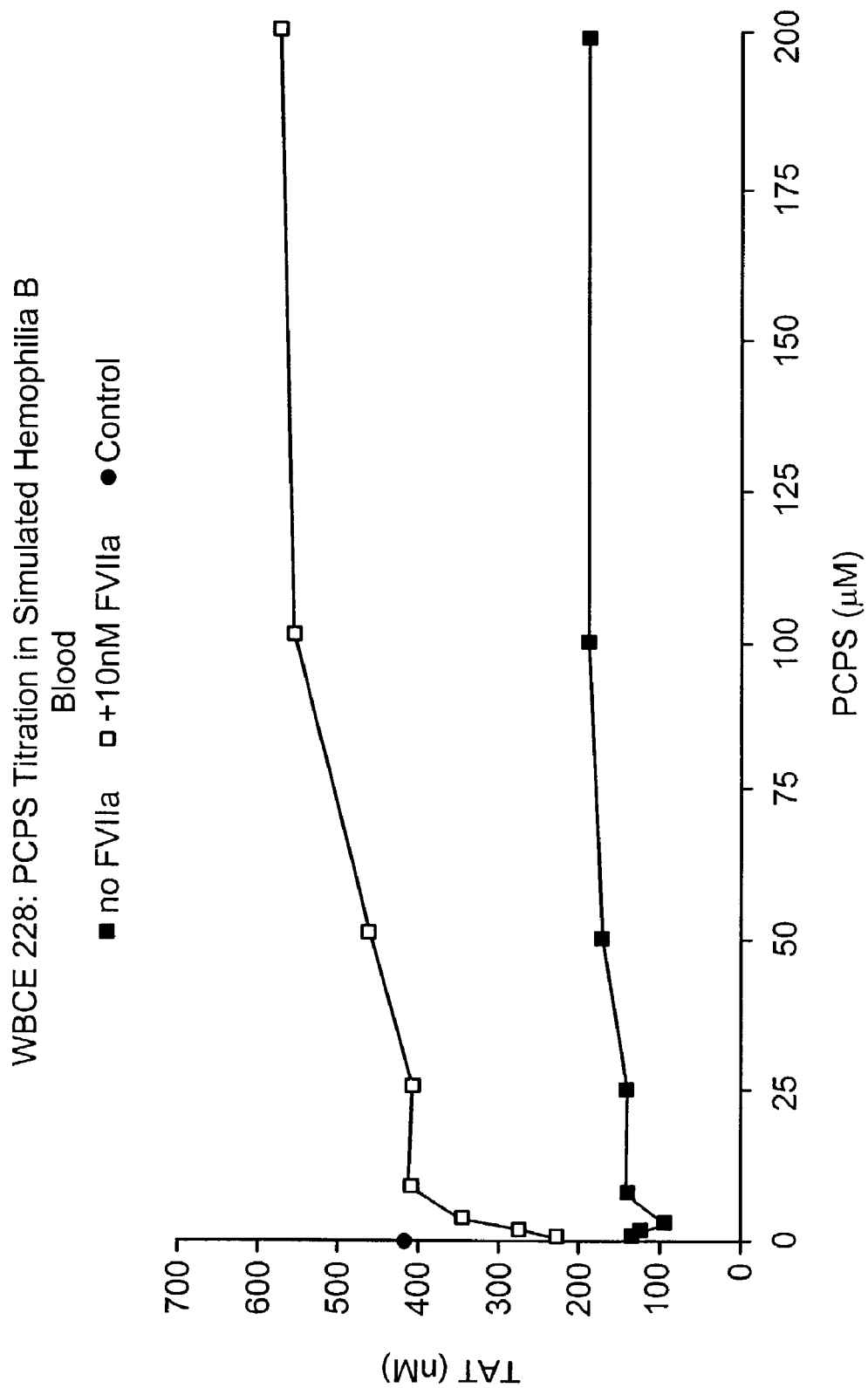
FIG. 3C is a graph which demonstrates the results obtained when hemophilia B blood is treated with PCPS and factor VIIa. Addition of 10 nM factor VIIa+PCPS to hemophilia A blood corrects thrombin generation at approximately 10 $\mu$M PCPS (open squares). PCPS alone has almost no effect on thrombin generation (filled squares).

Clotting in freshly drawn, non-anticoagulated whole blood was performed in 32 tubes (two series per experiment—16 tubes/series). All tubes were loaded with corn trypsin inhibitor (100 µg/ml blood), 12.5 pM relipidated TF/ml blood (PCPS:TF=2,000) and 50 µg/ml anti-factor IX antibody (antibody was not loaded into one normal control tube) in HBS with 2 mM CaCl$_2$, 10 nM recombinant factor VIIa and varying concentrations of PCPS (0–200 µM) (all tubes, experiment series only) and equivalent volume factor VIIa dilution buffer (HBS, pH 7.4) and PCPS (all tubes control series only). No more than 35 µl of reagents were loaded in each tube. Normal donor blood was drawn by venipuncture, delivered into the reagent-loaded tubes, and the clotting time was observed visually by two observers. Tubes were quenched with EDTA and FPRck in 10 min after clot formation. Tubes were centrifuged and the supernatants were aliquoted for TAT analyses. The results are shown in FIG. 3C, wherein, (•) represents normal control; (■) represents induced hemophilia B with PCPS addition; and, (□) represents induced hemophilia B with 10 nM factor VIIa and PCPS addition.

EXAMPLE 3

Factor VIIa Titration in Factor VIII Deficient Plasma

Figure 4:
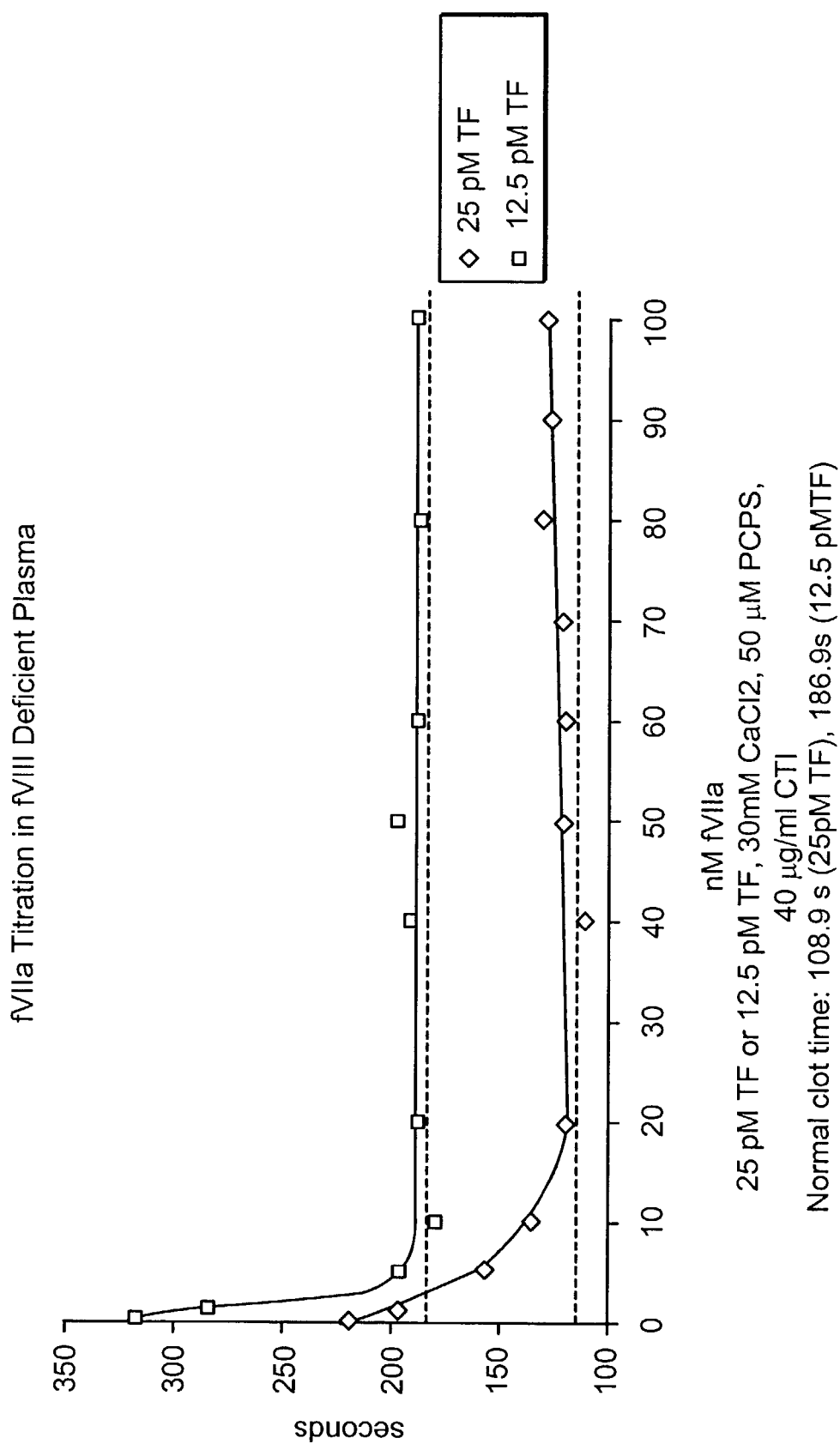
FIG. 4 is a graph which shows TF initiated clotting of corn trypsin inhibitor (CTI) inhibited factor VIII deficient plasma in the presence of 50 $\mu$M of PCPS. An increasing concentration of recombinant factor VIIa decreases clotting time to that of normal plasma (dotted lines).

Factor VIIa at varying concentrations (0–100 nM), 40 µg/ml CTI, 50 µM PCPS, and 30 mM CaCl$_2$ were added to the factor VIII deficient plasma pre-warmed to 37° C. Clotting was initiated by the addition of 12.5 pM (■) or 25 pM (♦) TF. Dotted lines represent clotting time of normal plasma initiated by corresponding concentration of TF and without factor VIIa addition. The results are shown in FIG. 4.

EXAMPLE 4

Thrombin Generation in the Synthetic "Plasma" in the Presence of Platelets

Figure 5:
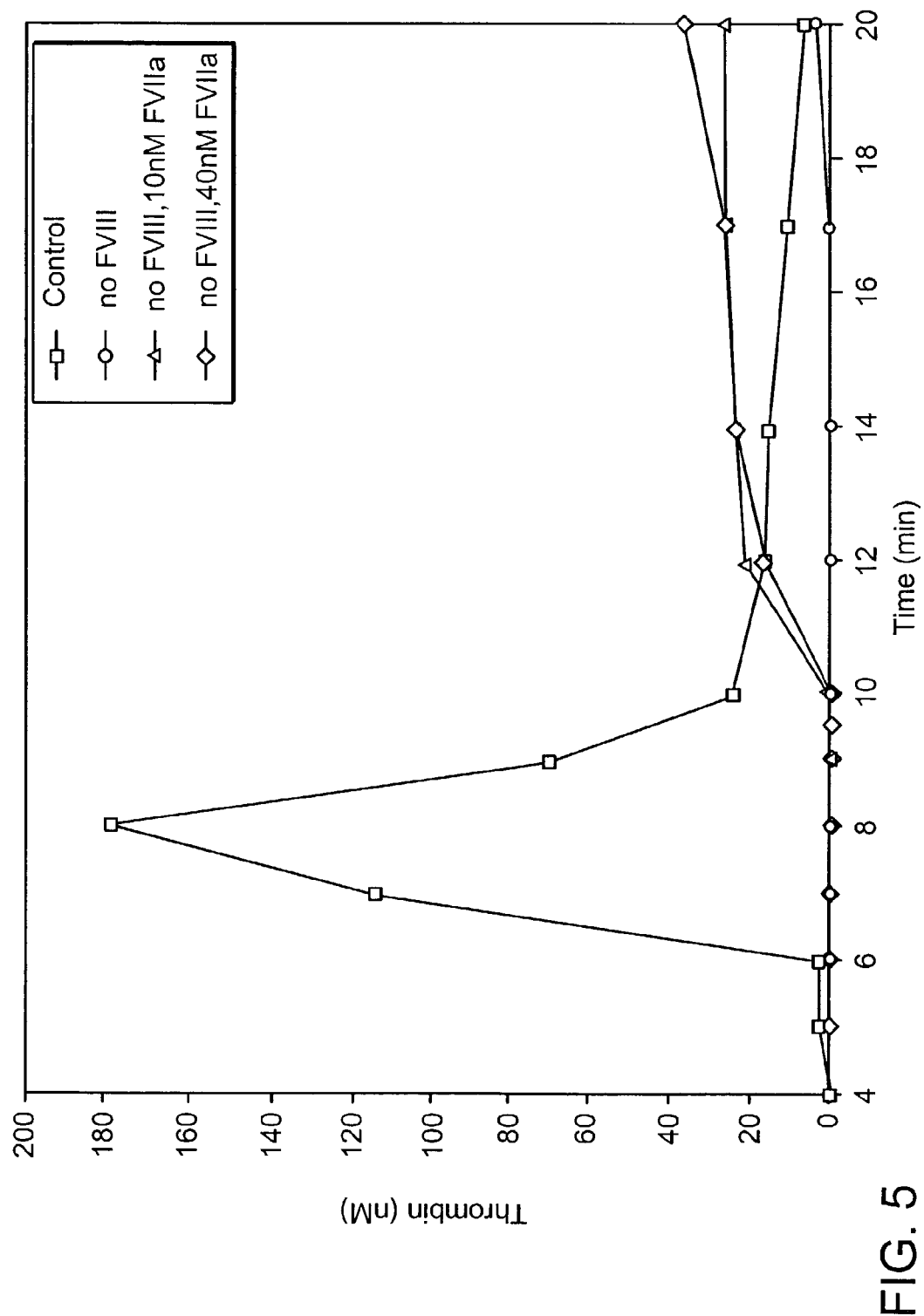
FIG. 5 is a graph showing thrombin generation in synthetic "plasma" initiated with 25 pM relipidated TF in the presence of washed platelets at physiological concentrations. Factor VIIa at 10–40 nM is not able to restore thrombin generation in hemophilia A.

In the control experiment (■), relipidated TF (PCPS:TF=2,000) at a concentration of 50 pM was incubated in HBS, 2 mM CaCl$_2$ for 10 min at 37° C. Factor V (40 nM), factor VIII (1.4 nM), and platelets (4×10$^8$/ml; 2 × mean physiological concentration) were added to the relipidated TF, and thrombin generation was started by addition of an equal volume of zymogen-inhibitor mixture containing prothrombin (2.8 µM), factors VII (20 nM), VIIa (0.2 nM), X (340 nM) and IX (180 nM), TFPI (5 nM), and AT-III (6.8 µM) prepared in HBS, 2 mM CaCl$_2$ and preheated at 37° C. for 3 minutes. The final concentrations of the proteins and platelets in the reaction represent mean physiological values. Final concentration of TF was 25 pM. Following initiation of the reaction, at selected time points, 10 µl aliquots were withdrawn from the reaction mixture and quenched in 20 mM EDTA in HBS (pH 7.4) containing 0.2 mM Spectrozyme TH and assayed immediately for thrombin activity. The hydrolysis of the substrate was monitored by the change in absorbance at 405 nm using a Molecular Devices $V_{max}$ spectrophotometer. Thrombin generation was calculated from a standard curve prepared by serial dilutions of α-thrombin. Results are shown in FIG. 5 wherein factor VIII was omitted (hemophilia A situation), and additional amounts of factor VIIa were added: (•) represents hemophilia control—no additional factor VIIa; (▲) represents 10 nM factor VIIa; and, (♦) represents 40 nM factor VIIa.

EXAMPLE 5

Thrombin Generation in the Synthetic "Plasma" in the Presence of 2 μM PCPS

Figure 6:
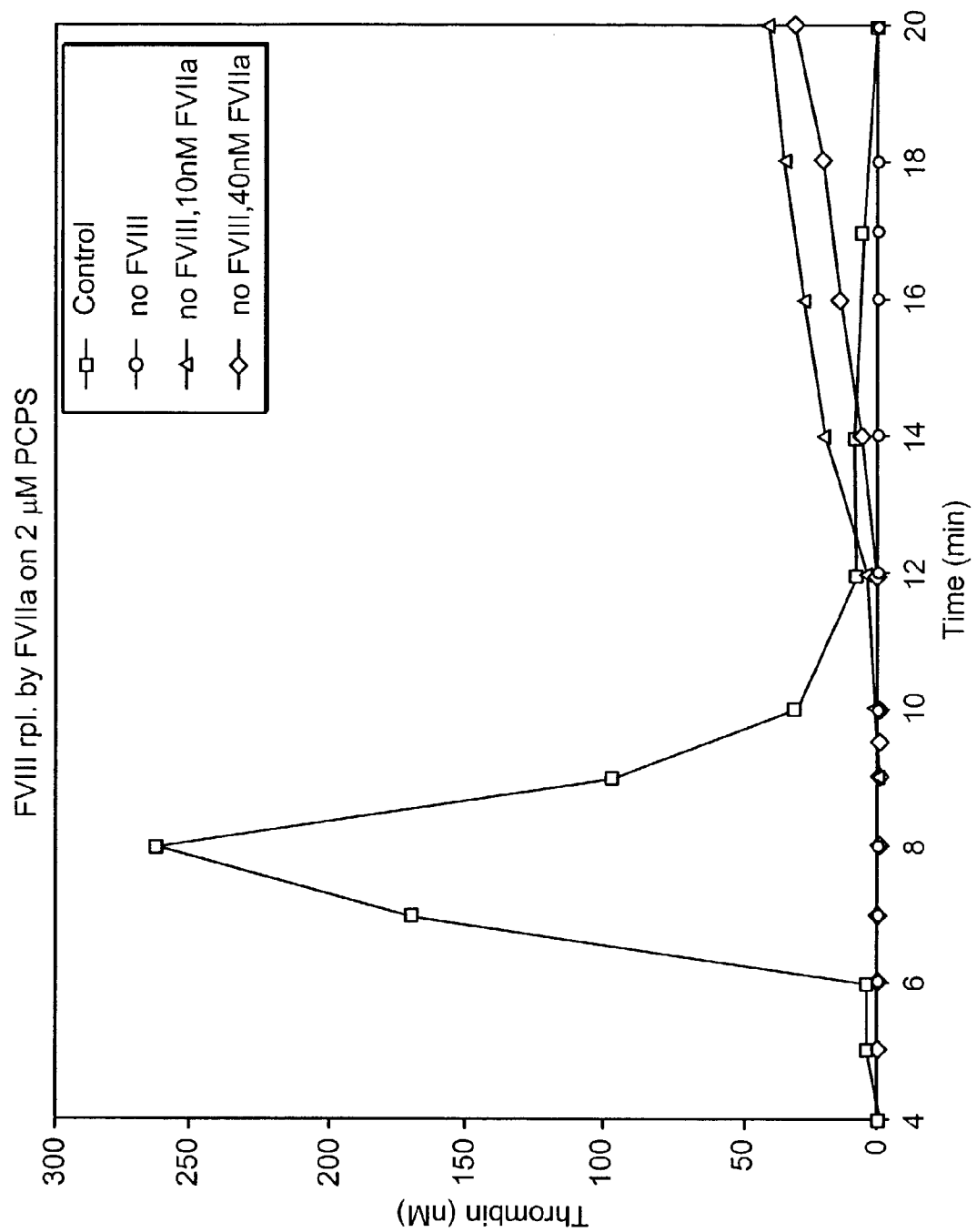
FIG. 6 is a graph demonstrating that when platelets in a synthetic "plasma" experiment are replaced with 2 $\mu$M PCPS, factor VIIa is unable to restore normal thrombin generation, in the absence of factor VIII (hemophilia A).

In the control experiment (■), relipidated TF (PCPS:TF=2,000) at a concentration of 50 pM was incubated with 4 μM PCPS in HBS, 2 mM $CaCl_2$ for 10 min at 37° C. Factor V (40 nM) and factor VIII (1.4 nM) were added to TF, and thrombin generation was started by addition of an equal volume of zymogen-inhibitor mixture containing prothrombin (2.8 μM), factors VII (20 nM), VIIa (0.2 nM), X (340 nM) and IX (180 nM), TFPI (5 nM), and AT-III (6.8 μM) prepared in HBS, 2 mM $CaCl_2$ and preheated at 37° C. for 3 minutes. The final concentrations of the proteins in the reaction represent mean physiological values. Final concentration of TF was 25 pM. Final concentration of PCPS was 2 μM. Following initiation of the reaction, at selected time points, 10 μl aliquots were withdrawn from the reaction mixture and quenched in 20 mM EDTA in HBS (pH 7.4) containing 0.2 mM Spectrozyme TH and assayed immediately for thrombin activity. The hydrolysis of the substrate was monitored by the change in absorbance at 405 nm using a Molecular Devices $V_{max}$ spectrophotometer. Thrombin generation was calculated from a standard curve prepared by serial dilutions of α-thrombin. The results are shown in FIG. 6, wherein factor VIII was omitted (hemophilia A situation), and additional amounts of factor VIIa were added: (•) represents hemophilia control—no additional factor VIIa; (▲) represents 10 nM factor VIIa; and, (♦) represents 40 nM factor VIIa.

EXAMPLE 6

Thrombin Generation in the Synthetic "Plasma" at Varying PCPS Concentrations

Figure 7A:
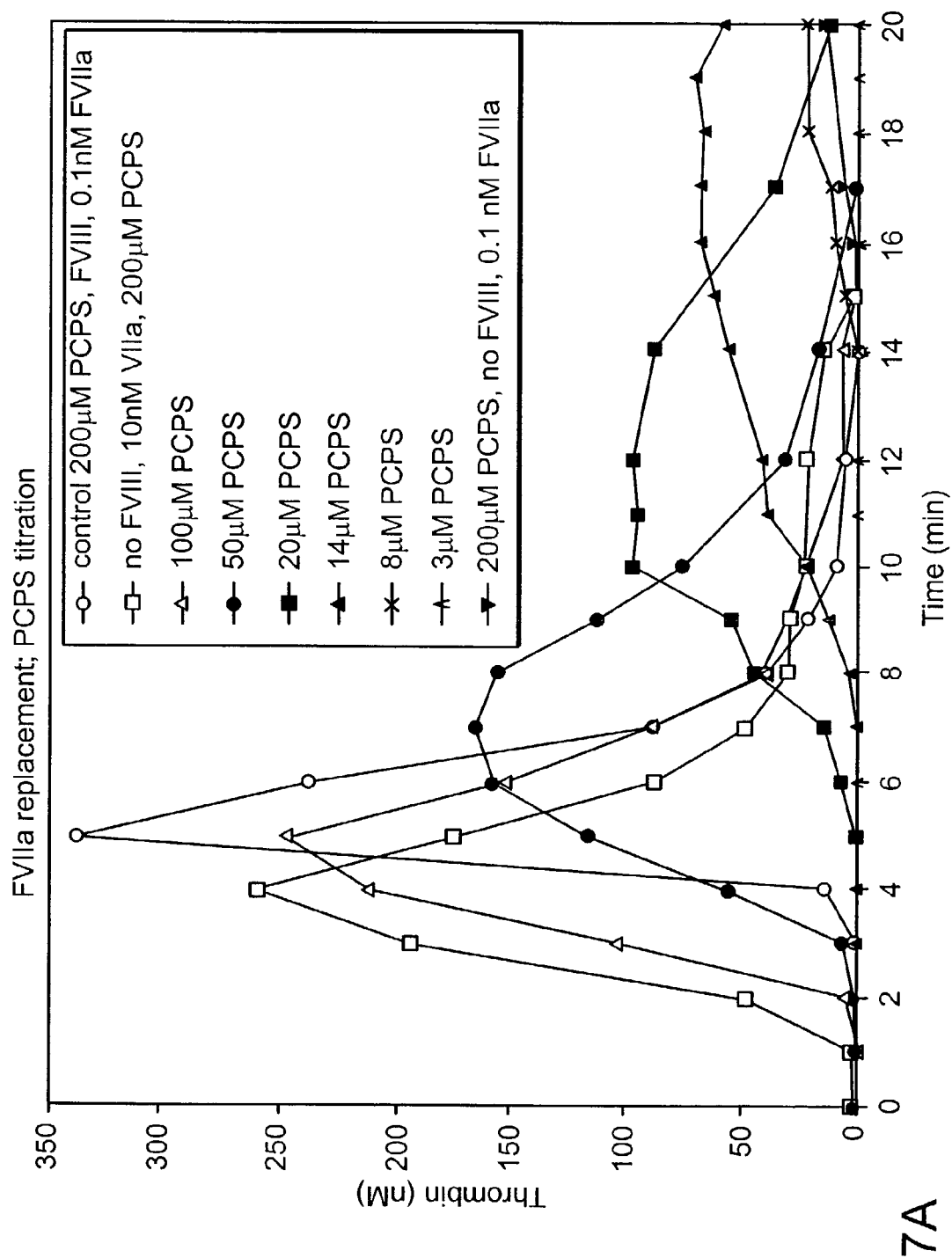
FIGS. 7A–D are graphs which demonstrate a synthetic "plasma" experiment initiated with 12.5 pM relipidated TF. Thrombin generation was not observed in the absence of factor VIII and in the presence of 10 nM of factor VIIa when PCPS was present at 3 $\mu$M or below. Thrombin generation is restored to normal at 50–100 $\mu$M PCPS.
Figure 7B:
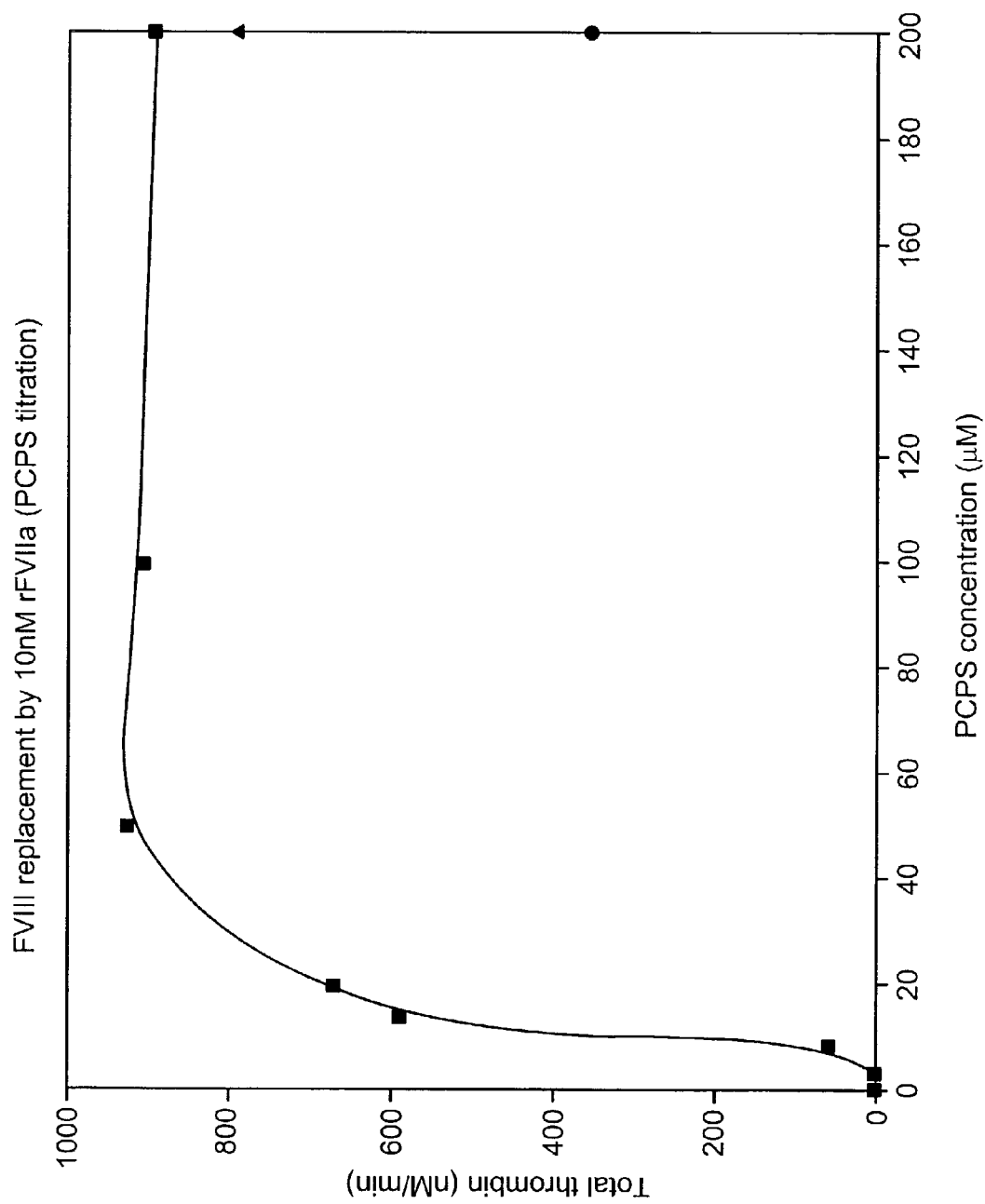
Figure 7C:
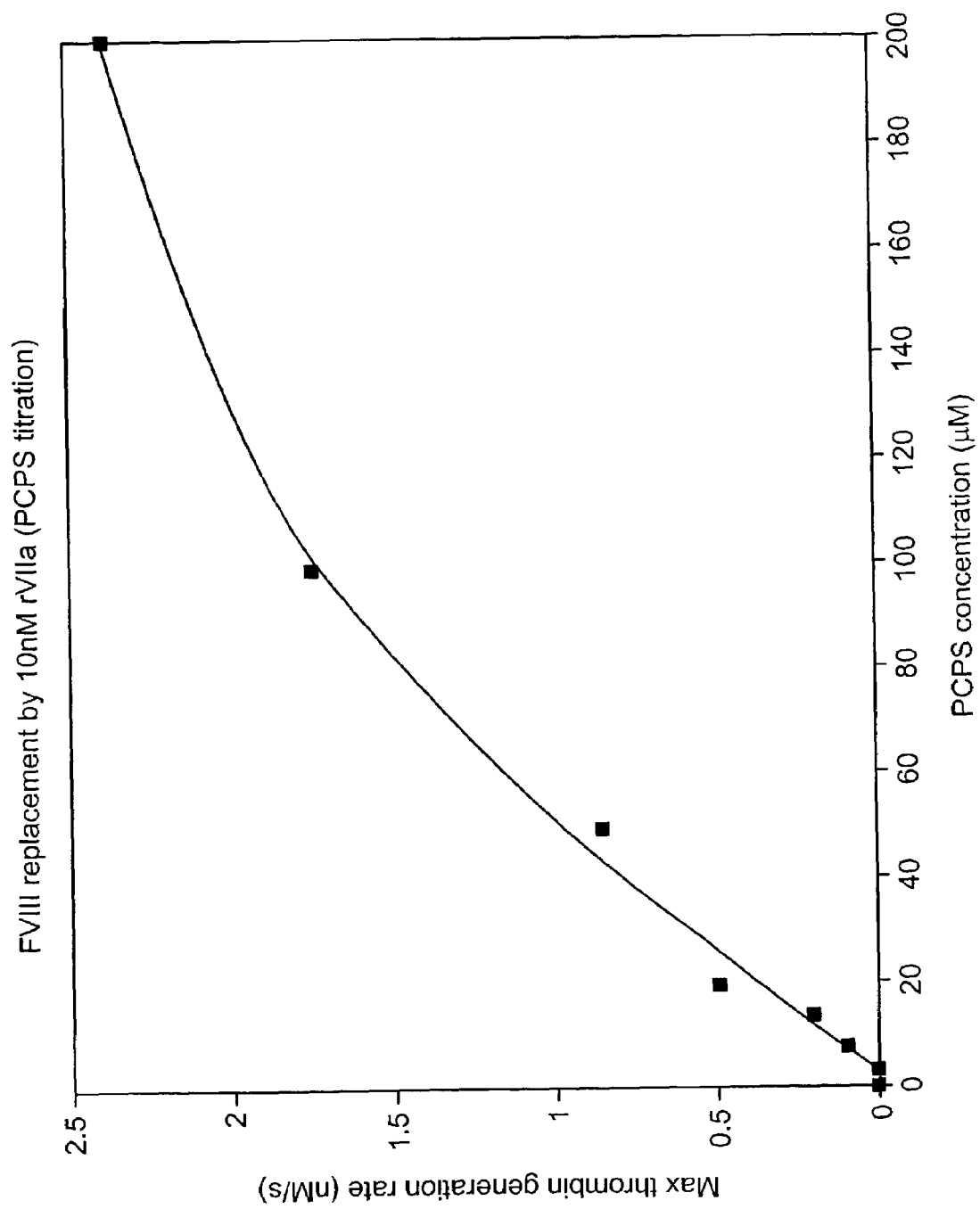
Figure 7D:
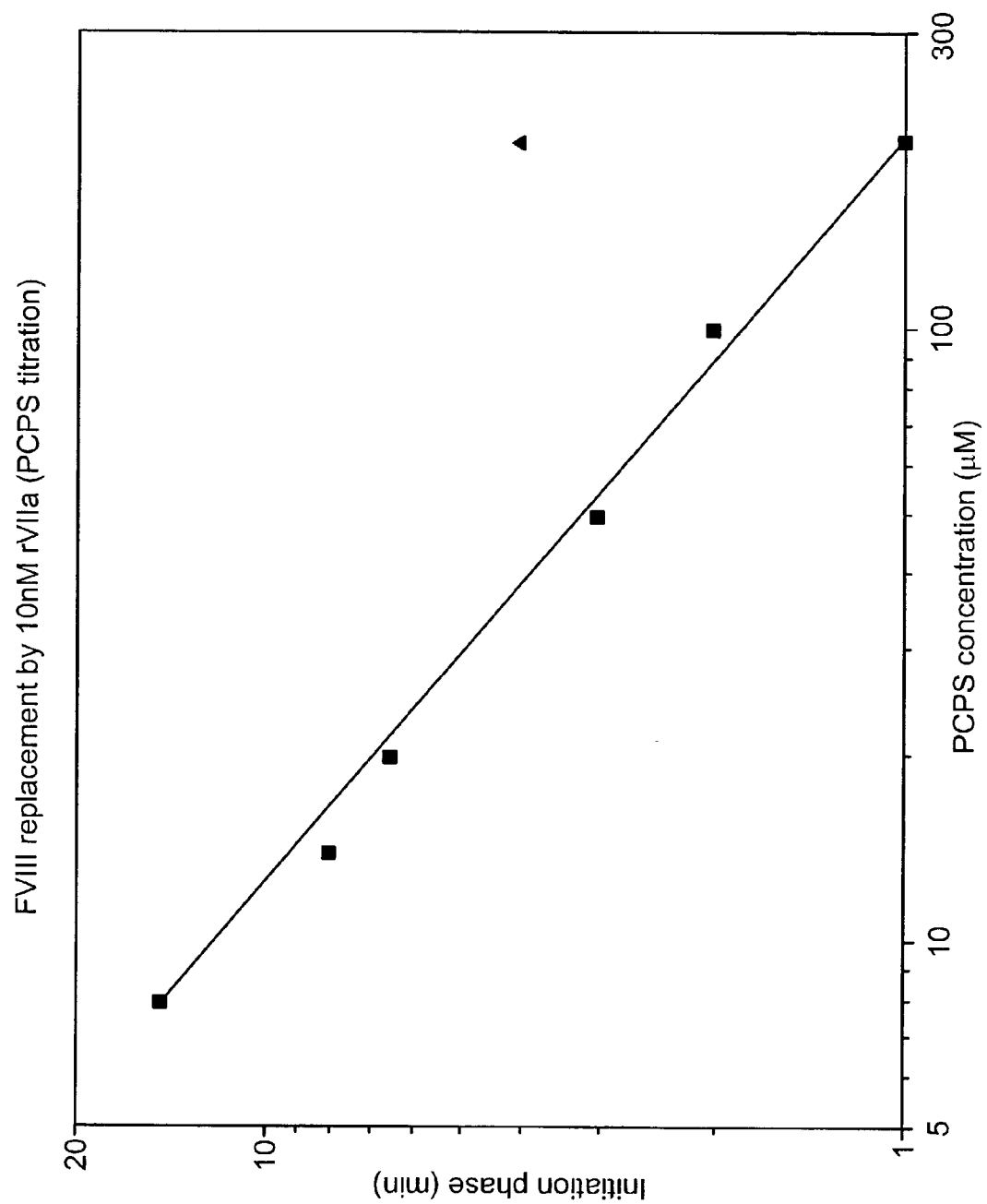

In the control experiment (FIG. 7A; O), relipidated TF (PCPS:TF=2,000) at a concentration of 25 pM was incubated with 400 μM PCPS in HBS, 2 mM $CaCl_2$ for 10 min at 37° C. Factor V (40 nM) and factor VIII (1.4 nM) were added to TF, and thrombin generation was started by addition of an equal volume of zymogen-inhibitor mixture containing prothrombin (2.8 μM) factors VII (20 nM), VIIa (0.2 nM), X (340 nM) and IX (180 nM), TFPI (5 nM), and AT-III (6.8 μM) prepared in HBS, 2 mM $CaCl_2$ and preheated at 37° C. for 3 minutes. The final concentrations of the proteins in the reaction represent mean physiological values. Final concentration of TF was 12.5 pM. Final concentration of PCPS was 200 μM. Following initiation of the reaction, at selected time points, 10 μl aliquots were withdrawn from the reaction mixture and quenched in 20 mM EDTA in HBS (pH 7.4) containing 0.2 mM Spectrozyme TH and assayed immediately for thrombin activity. The hydrolysis of the substrate was monitored by the change in absorbance at 405 nm using a Molecular Devices $V_{max}$ spectrophotometer. Thrombin generation was calculated from a standard curve prepared by serial dilutions of α-thrombin. The total active thrombin generated was evaluated by integrating the area under thrombin vs time curve. The rest of experiments (FIG. 7) were conducted in the absence of factor VIII (hemophilia A situation) and in the presence of factor VIIa at 0.1 nM (physiological concentration) and PCPS at 200 μM (▼) or in the presence of factor VIIa at 10 nM and PCPS at 3 μM (*), 8 mM (x), 14 μM (▲), 20 μM (■), 50 μM (•), 100 μM (Δ), and 200 μM (□). Parameters of thrombin generation presented in FIGS. 7B, 7C, and 7D are calculated from FIG. 7A data.

EXAMPLE 7

Figure 8:
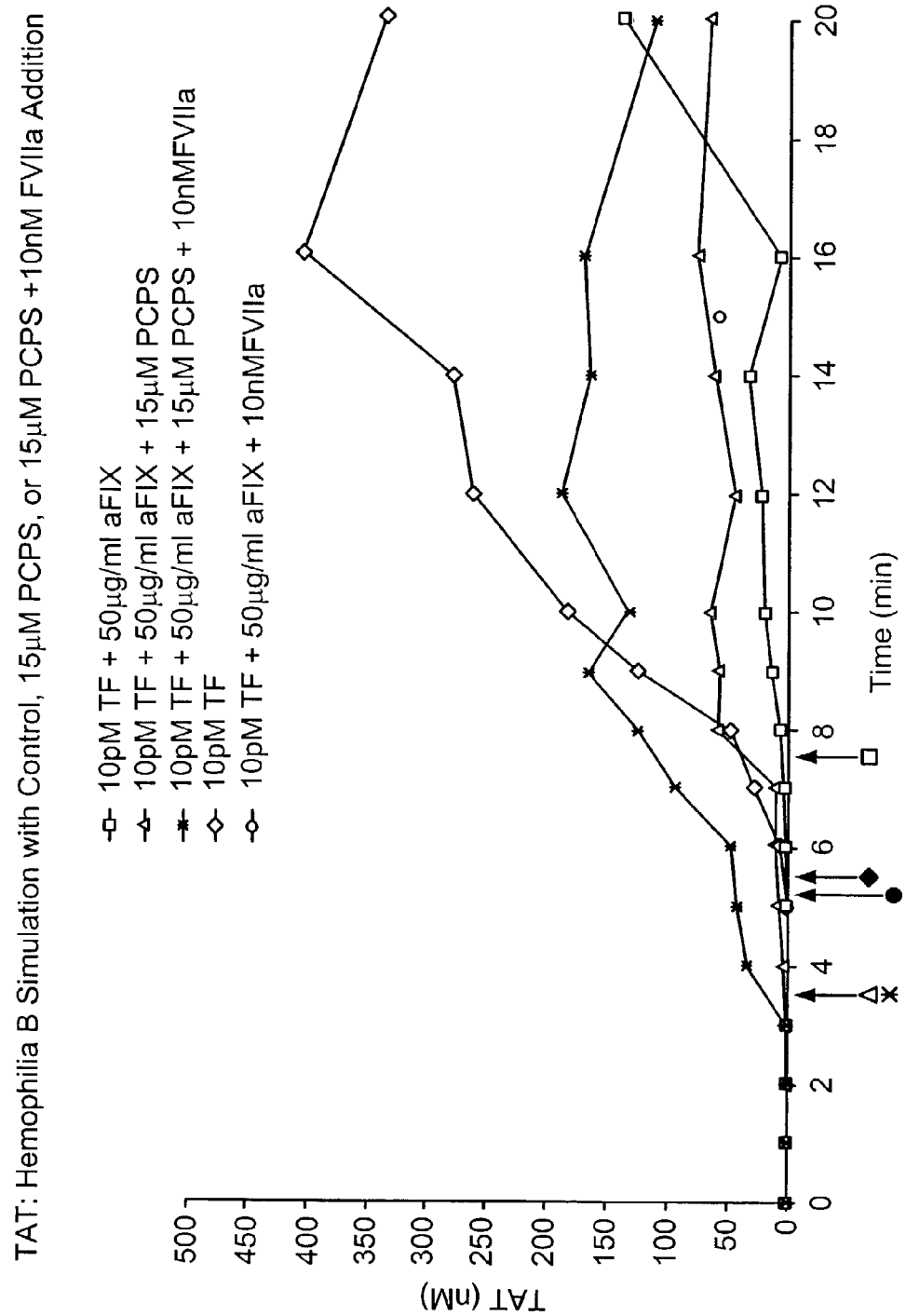
FIG. 8 is a graph showing the results obtained on thrombin generation in induced hemophilia B blood in the presence of 10 nM factor VIIa and 15 $\mu$M PCPS.

The Influence of 10 nM Factor VIIa and 15 μM PCPS on Thrombin Generation in Whole Blood Clotting in freshly drawn, non-anticoagulated whole blood was performed in 64 tubes (four series per experiment—16 tubes/series). All tubes were loaded with corn trypsin inhibitor (100 μg/ml blood), 10 pM relipidated TF (PCPS:TF=2,000) in HBS with 2 mM $CaCl_2$ (all tubes in each series except phlebotomy control tube), anti-factor IX antibody (50 μg/ml blood) (all tubes, three experiment series only), 10 nM recombinant factor VIIa (all tubes, one experiment series only), 15 μM PCPS (all tubes, two experiment series only), and equivalent volume of factor VIIa, PCPS, and anti-factor IX antibody dilution buffer (HBS, pH 7.4, all tubes not loaded with corresponding adjuvants). No more than 35 μl of reagents were loaded in each tube. The zero tube of each series was pretreated using 1 ml of 50 mM EDTA and 10 μl of 10 mM FPRck (diluted in 0.01 M HCl). Normal donor blood was drawn by venipuncture, delivered into the reagent-loaded tubes, and the tubes were periodically quenched with EDTA and FPRck. The clotting time was observed visually by two observers. Tubes were centrifuged and the supernatants were aliquoted for further TAT analyses. The results are shown in FIG. 8, wherein (♦) represents normal control (no anti-factor IX antibody); (■) represents induced hemophilia B (50 μg/ml anti-factor IX antibody); (Δ) represents induced hemophilia B with 15 μM PCPS addition; (X) represents induced hemophilia B with 15 mM PCPS and 10 nM factor VIIa addition; and, (•) represents induced hemophilia B with 10 nM factor VIIa addition.

EXAMPLE 8

Hemophilia Treatment with Recombinant Factor VIIa and Synthetic Phospholipids

Several models of blood coagulation were used to examine hemophilia A treatment with recombinant factor VIIa.

In one of them, synthetic "plasma" mixtures were prepared with purified proteins involved in blood coagulation and its regulation. Synthetic phospholipids (PCPS; 75% phosphatidylcholine and 25% phosphatidylserine) or washed platelets were also present. At selected time points samples of the reaction mixture were taken and analyzed for thrombin generation.

In the second model, fresh whole blood was added to tubes containing corn trypsin inhibitor (CTI; prevents contact pathway-initiated coagulation) and TF. At selected time points blood in the tubes is quenched and samples are analyzed.

In both these models, the procoagulant process may be divided into two phases: an INITIATION PHASE and a PROPAGATION PHASE (FIG. 1). The INITIATION PHASE is characterized by the appearance of nanomolar amounts of thrombin, femto- and picomolar amounts of other coagulation enzymes and the activation of pro-cofactors factors V and VIII. The PROPAGATION PHASE is characterized by explosive, extensive prothrombin activation.

Figure 2:
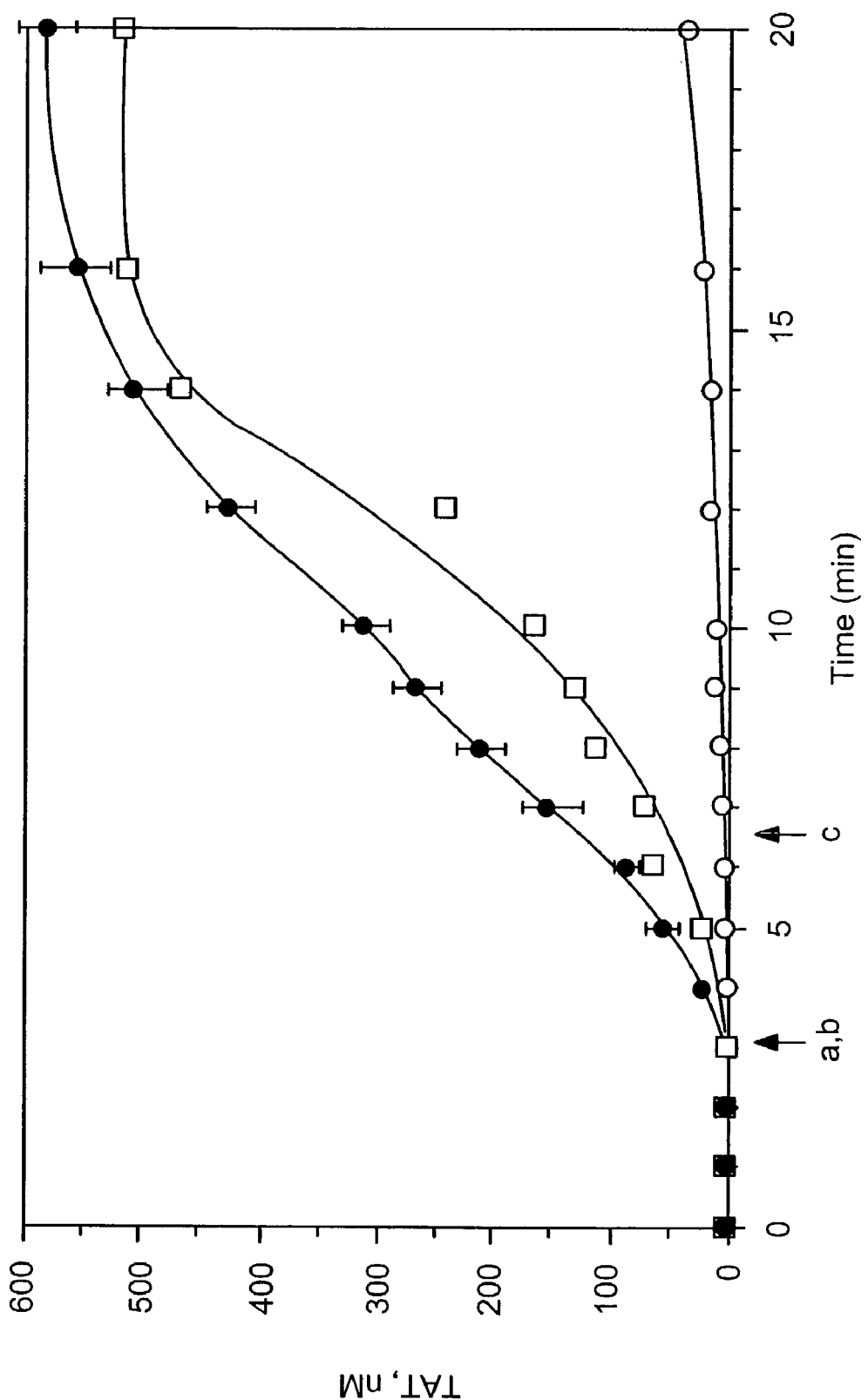
FIG. 2 is a graph showing that the blood clotting time corresponds to the beginning of the propagation phase—arrow "a" and filled circles; thrombin generation is evaluated as thrombin-antithrombin-III complex (TAT) formation. In hemophilia A blood, the clotting time (initiation phase) is slightly prolonged (arrow "c"), however, the bolus of thrombin (TAT) produced during the propagation phase does not occur (open circles). The addition of factor VIII corrects the clotting time (arrow "b") and restores the propagation phase of thrombin generation (open squares).

In the whole blood model, when normal blood was used, clotting time corresponded to the beginning of the PROPAGATION PHASE [FIG. 2, arrow "a" and filled circles; thrombin generation is evaluated as thrombin-antithrombin-III complex (TAT) formation]. In hemophilia A blood, the clotting time (INITIATION PHASE) was slightly prolonged (arrow "c"), however, the bolus of thrombin (TAT) produced during the PROPAGATION PHASE did not occur (open circles). The addition of factor VIII restored the clotting time (arrow "b") and the PROPAGATION PHASE of thrombin generation (open squares). When factor VIIa at a final concentration of 10 nM was added in vitro to CTI-inhibited fresh blood of a hemophilia A patient whose factor VIII level was <1% and blood coagulation was initiated by 12.5 pM TF, clotting occurred 3:20 min after initiation. In the control experiment (without factor VIIa addition) the clotting time of the same blood was 6:25 min. Blood taken from a healthy volunteer under the same conditions clotted at 3:15 min after initiation. When 10 nM factor VIIa was added to the normal blood, the clotting time was shortened to 1:53 min (FIG. 3A, arrows indicate clotting time). Thus, 10 nM recombinant factor VIIa was able to correct the visually observed clotting time of hemophilia A blood. However, the thrombin generation (FIG. 3A; diamonds) analyses showed that thrombin generation was barely elevated by the addition of factor VIIa to the hemophilia A blood compared to blood without factor VIIa addition (FIG. 3A; circles), i.e., no PROPAGATION PHASE in both cases. TAT levels in the blood of a normal person without factor VIIa addition, reach significantly higher levels (FIG. 3A; squares) than in hemophilia A blood with factor VIIa addition. Similarly, the addition of factor VIIa had no effect on the solid clot formation (FIG. 3B; compare middle and bottom panels). However, the addition of 10 nM factor VIIa together with PCPS to the hemophilia blood corrects thrombin generation at approximately 10 µM PCPS (FIG. 3C; compare open squares and filled circle). PCPS alone (without factor VIIa addition) has almost no effect on thrombin generation (FIG. 3C; filled squares).

TF initiated clotting of CTI inhibited factor VIII deficient plasma showed that an increasing concentration of recombinant factor VIIa decreased clotting time to that of normal plasma (FIG. 4; dotted lines). Saturation was achieved at approximately 10 nNM factor VIIa in the presence of 50 µM PCPS.

Thrombin generation in synthetic "plasma" initiated with 25 pM relipidated TF and in the presence of washed platelets at physiological concentration is shown in FIG. 5. Squares represent a complete system with all procoagulants present at physiological concentrations.

Thrombin generation in the absence of factor VIII (circles) was suppressed. Factor VIIa at 10 nM slightly increased thrombin generation, however it was not able to restore normal thrombin levels or the duration of the INITIATION PHASE (triangles). A further increase in factor VIIa concentration to 40 nM did not increase thrombin generation (diamonds). In a similar synthetic plasma experiment, when platelets were replaced by 2 µM PCPS (this concentration is equivalent to the contribution of normal platelets when the latter are present at physiological concentration), neither 10 nM nor 40 nM factor VIIa was able to restore normal thrombin generation (FIG. 6). In a synthetic plasma mixture initiated with 12.5 pM relipidated TF, thrombin generation was not detectable in the absence of factor VIII and in the presence of 10 nM factor VIIa when PCPS was present at 3 µM or below (FIG. 7A; stars). Increasing the PCPS concentration increased the total thrombin generated (integrated area under the thrombin generation curve) (FIG. 7B) and the maximum thrombin generation rate (FIG. 7C) and decreased the duration of the INITIATION PHASE (FIG. 7D). In the absence of factor VIII and in the presence of 10 nM factor VIIa, the normal levels of total thrombin generated and the duration of the INITIATION PHASE (similar to those achieved in the presence of physiological concentrations of factors VIII and VIIa; open circles in FIG. 7A, filled triangles in FIGS. 7B and 7D) were achieved at ~50 µM PCPS. Total thrombin generated in the presence of platelets in a complete system is indicated by the filled circle, and in the absence of factor VIII by the open circle (FIG. 7B).

EXAMPLE 9

Factor VIIa and Phospholipid Influence on Coagulation in "Acquired" Hemophilia

Materials and Methods

Human coagulation factors VII, X, IX, and prothrombin, were isolated from fresh frozen plasma using the general methods of Bajaj et al.[3] and were purged of trace contaminants and traces of active enzymes as described[4]. Human factor V and AT-III were isolated from freshly frozen plasma[5,6]. Recombinant factor VIII and recombinant tissue factor (TF) (residues 1–242) were provided as gifts from Drs. Shu Len Liu and Roger Lundblad (Hyland division, Baxter Healthcare Corp, Duarte, Calif.). Recombinant human factor VIIa was purchased from NOVO Pharmaceuticals (Copenhagen, Denmark). Recombinant full-length TFPI produced in *Escherichia coli* was provided as a gift by Dr. Kirk Johnson (Chiron Corp, Emeryville, Calif.). The TF/lipid reagent (2 nM/10µM) and corn trypsin inhibitor (CTI) were prepared as described[7]. Phosphatidylserine (bovine brain) (PS), phosphatidylcholine (egg yolk) (PC), and EDTA were purchased from Sigma (St Louis, Mo.). Phospholipid vesicles (PCPS) composed of 25% PS and 75% PC were prepared as described[15]. Spectrozyme TH was purchased from American Diagnostica, Inc (Greenwich, Conn.). D-Phe-Pro-ArgCH$_2$Cl (FPRck) was synthesized in house. ELISA thrombin-AT-III (TAT) kit (Enzygnost TAT) was purchased from Behring (Marburg, Germany). Monoclonal anti-factor IX antibody (α-FIX-91) was obtained from the Biochemistry Antibody Core Laboratory (University of Vermont). Fibrinogen, fibrinopeptides A (FPA) and B (FPB), and solid clot analyses were performed as described[2].

Determination of Active TF in TF/PCPS Preparations

Relipidated TF (TF/PCPS: 200 pM/400 nM) and varying concentrations of recombinant factor VIIa (0–600 pM) were incubated at 37° C. in HBS, 2 mM CaCl$_2$, 0.1% PEG, pH 7.4 containing 10 µM PCPS for 10 min. Factor X at 170 nM concentration was added and 20 µl aliquots were removed every 30 s for 5 min and quenched into 160 µl HBS containing 20 mM EDTA. 20 µl of 2 mM Spectrozyme Xa was added and the rate of substrate hydrolysis was estimated. Factor Xa generation rate was evaluated from a standard curve using serial dilutions of purified factor Xa. The concentration of active TF was estimated using a Scatchard plot (factor VIIa bound vs. bound/free ratio) assuming 1:1 stoichiometry for TF and factor VIIa.

Human Donors

Three healthy donors were recruited, advised according to a protocol approved by the University of Vermont Human Studies Committee[16,7] and their consent to participate obtained. Donors with history of thrombosis/hemorrhage, or regular aspirin or drug use were excluded. All individuals exhibited normal values for the PT (11.6–13.0 s), INR (1.0–1.1), fibrinogen (2.4–3.4 mg/ml) and blood coagulation protein levels, and platelet counts (1.8–2.7×10$^8$/ml).

"Acquired" Hemophilia B Blood

An in vitro equivalent of natural acquired hemophilia B was manufactured in fresh CTI-inhibited normal whole blood by the addition of 50 μg/ml α-FIX-91. At this concentration, the antibody prolonged the aPTT of normal plasma from 38 to 115 s. The aPTT of commercial factor IX-deficient plasma (<1% of factor IX; George King) was 112 s. The "titer" of the α-IX-91 at 50 μg/ml was 27 Bethesda units. Purified plasma factor IX addition returned the aPTT to 39 s.

Synthetic Coagulation Model

The procedure used is a modification of Lawson et al.[17] and van't Veer et al.[4] and involves mixing proteins, lipids, platelets and relipidated TF to produce the equivalent of a thrombin-generating "synthetic plasma".

I. Procofactor solution: Relipidated TF (20 pM) was incubated with 4 μM PCPS (when desired, additional amounts of PCPS (6–400 μM) were added) in HBS, 2 mM CaCl$_2$ for 10 min at 37° C. Factor V (40 nM) and factor VIII (1.4 nM) were added to the relipidated TF prior to the initiation.

II. Zymogen-inhibitor solution: Prothrombin (2.8 μM), factors VII (20 nM), VIIa (0.2 nM), X (340 nM) and IX (180 nM), TFPI (5 nM), and AT-III (6.8 μM) were incubated in HBS, 2 mM CaCl$_2$ on ice for 7 min and the preheated at 37° C. for 3 min.

The reaction was started by mixing equal volumes of both solutions resulting in mean physiological concentrations of the proteins, with a final TF concentration of 10 pM. Following initiation of the reaction, at selected time points, 10 μl aliquots were withdrawn from the reaction mixture and quenched in 20 mM EDTA in HBS (pH7.4) containing 0.2 mM Spectrozyme TH and assayed immediately for thrombin activity. The hydrolysis of the substrate was monitored by the change in absorbance at 405 nm using a Molecular Devices $V_{max}$ spectrophotometer. Thrombin generation was calculated from a standard curve prepared by serial dilutions of α-thrombin.

TF-initiated Clotting of Fresh Human Blood

The protocol used is a modification of Rand et al.[16]. Clotting in freshly drawn, nonanticoagulated whole blood was performed in tubes placed on a rocking table at 37° C. and loaded with CTI (100 μg/ml blood).

I. Multiple-tube experiments: Experiments were performed in 4 series of tubes (16 tubes/series; 2 blood draws). 62 tubes (15 in each of 4 series and two supplementary) were loaded with CTI and 4 pM relipidated TF (PCPS:TF 5000) in HBS with 2 mM CaCl$_2$. Four phlebotomy control tubes (1 tube/series) contained no TF. 50 tubes (3 experimental series and supplementary) were loaded with 50 μg/ml of α-FIX-91. 16 of 50 tubes (first experimental series) had no additional reactants added, 16 (second experimental series) were loaded with 15 μM PCPS (final concentration after the addition of blood) and other 16 tubes (third experimental series) were loaded with 15 μM PCPS and 10 nM factor VIIa. Two supplementary tubes were loaded with 10 nM factor VIIa (no PCPS). No more than 35 μl of all reagents were loaded in each tube. The zero tube of each series was pretreated using 1 ml of 50 mM EDTA and 10 μl of 10 mM FPRck (diluted in 10 mM HCl). Normal blood was drawn by venipuncture, 1 ml aliquots were delivered into the reagent-loaded tubes, and the tubes were periodically quenched with EDTA and FPRck. The clotting time was observed visually by two observers. Two supplementary tubes were quenched 10 min after the clotting time. Tubes were centrifuged and the supernatants were aliquoted for further analyses. ELISA for TAT was performed. FPA and FPB release was evaluated by HPLC, fibrinogen depletion by Western blots. Solid clots were lyophilized, weighed, solubilized and analyzed by gel electrophoresis[2].

II. Single-tube experiments (PCPS titration): In these experiments all 41 tubes (10 tubes/series and phlebotomy control tube) were loaded with CTI and varying concentrations of PCPS in duplicates (0, 1, 3, 8, and 25 μM) (no PCPS in phlebotomy control tube). In control experiment one series of tubes was loaded with 5 pM TF alone (normal control), another one with 5 pM TF and 50 μg/ml of α-FIX-91 (hemophilia B control). In a second experiment all tubes were loaded with 50 μg/ml of α-FIX-91 and 10 nM factor VIIa. In one series TF was present in another absent. Fresh blood (1 ml) was delivered into reagent-loaded tubes. Tubes were quenched 10 min after the clotting time. ELISA for TAT was performed.

Results

PCPS Titration in the Synthetic Coagulation Model.

Figure 9A:
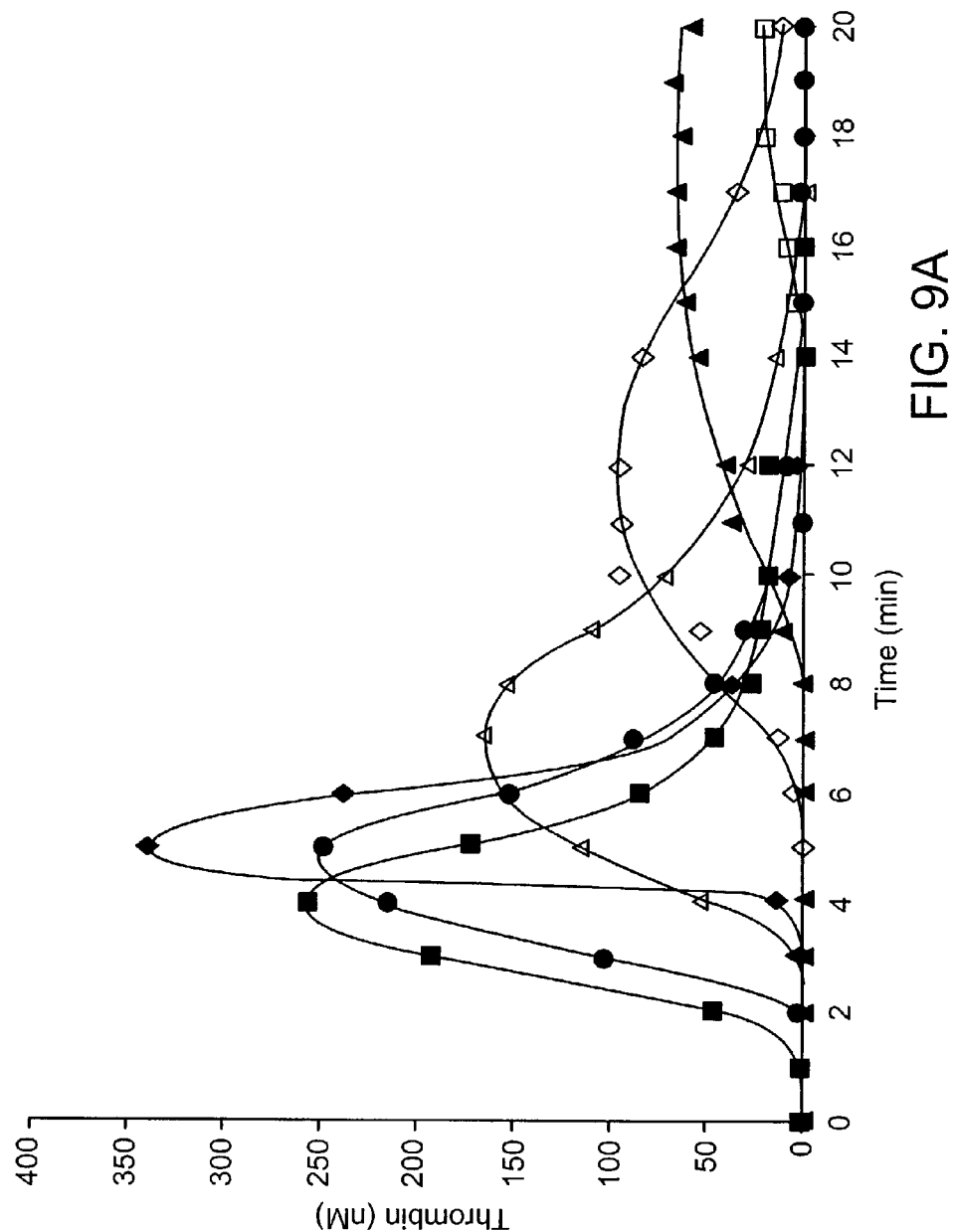
FIGS. 9A–9C are graphs showing thrombin generation in the synthetic coagulation model. Thrombin generation was induced with 10 pM relipidated TF either in the presence of 200 M PCPS and factors V, VIII, VII, VIIa, IX, and X, prothrombin, AT-III, and TFPI at physiological concentrations (♦) or in the presence of 200 M PCPS and in the absence of factor VIII ( ), or in the absence of factor VIII and in the presence of 10 nM factor VIIa and 0 (○), 14 (▲), 20 (◇), 50 (Δ), 100 (•) and 200 M (•) PCPS.
Figure 9B:
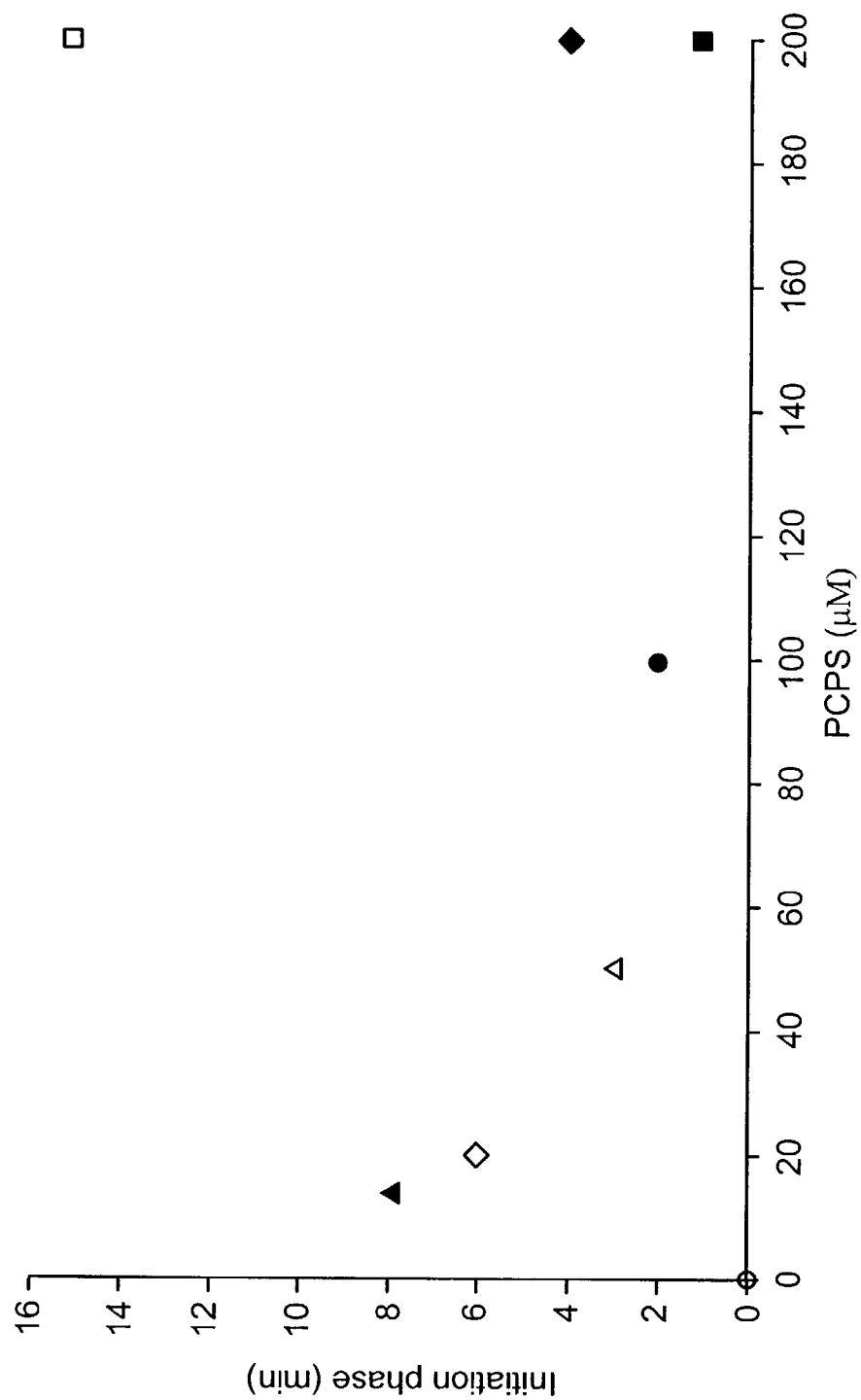
Figure 9C:
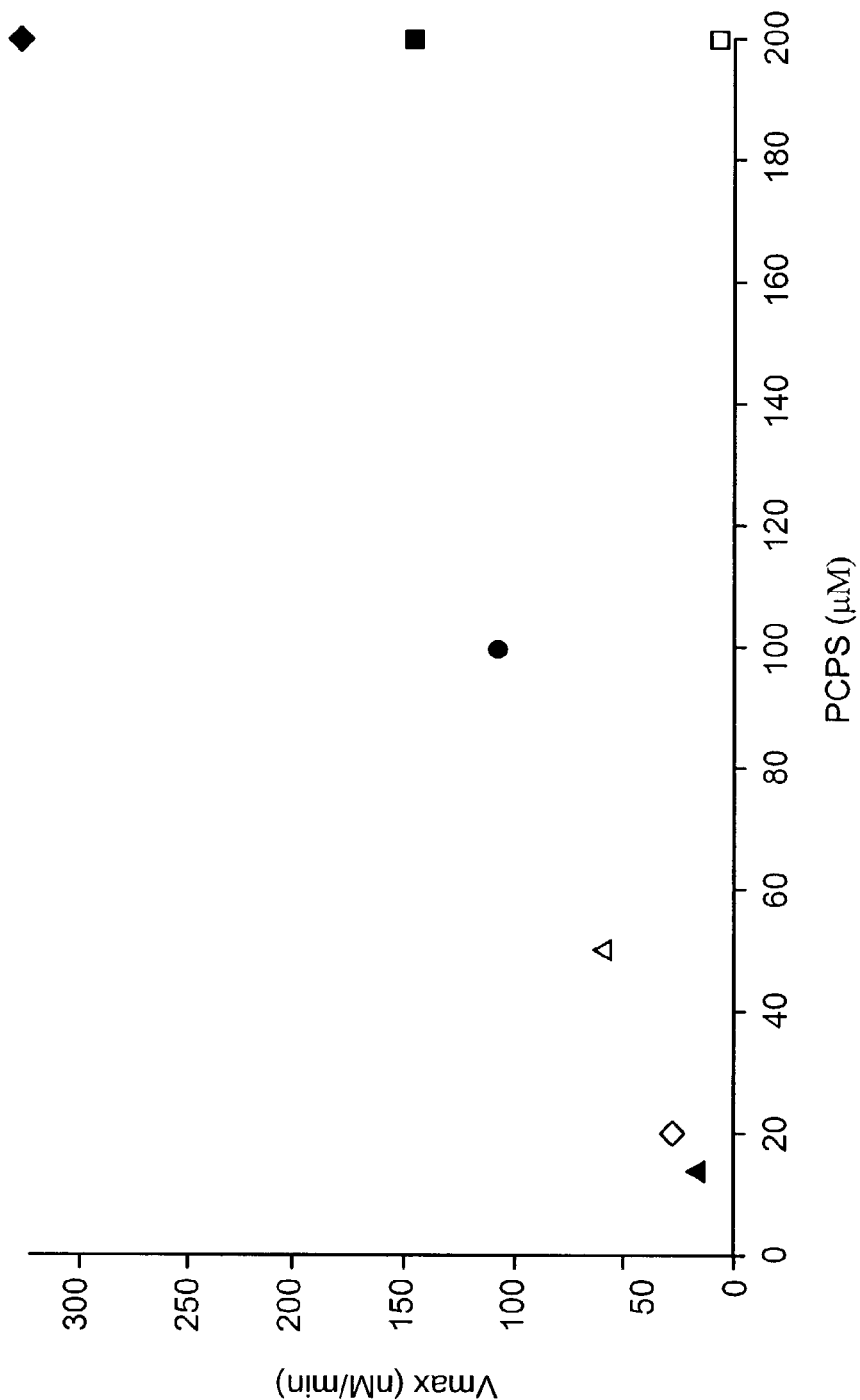

In all experiments of this series, the concentration of TF was 10 pM. Results are presented in FIGS. 9A–C. FIG. 9A depicts thrombin generation profiles over time at varying PCPS concentrations. Maximum rates of thrombin generation and the initiation phase duration dependence on the PCPS concentration (FIGS. 9B and C, respectively) are calculated from the data of FIG. 9A. In the control experiment (complete system) with 200 μM PCPS, thrombin was generated at a maximum rate of 320 nM/min after an initiation phase of ~4 min (♦). The highest level of thrombin observed was 340 nM. In the absence of factor VIII (approximation of hemophilia A) with 200 μM PCPS, the initiation phase was prolonged to 15 min (; FIG. 9B) and the maximum rate of thrombin generation was decreased to 6.2 nM/min (; FIG. 9C). Only 18 nM thrombin was detected after 20 min. The addition of 10 nM factor VIIa in the absence of factor VIII at 200 μM PCPS, decreased the initiation phase to 1 min (■; FIG. 9B) and increased the maximum thrombin generation rate to 140 nM/min (■; FIG. 9C). A decrease in PCPS to 100 μM had little effect on the maximum rate of thrombin generation during the propagation phase (110 nM/min) and maximum thrombin levels (~250 nM at both PCPS concentrations), while the initiation phase was prolonged to 2 min (•; FIG. 9B). Further reductions in PCPS concentration caused prolongation of the initiation phase and decreased rates of prothrombin activation during the propagation phase. At 50 μM PCPS (Δ) the initiation phase duration was similar to that of the normal control, while the maximum rate of thrombin generation was only 60 nM/min with the maximum thrombin level of 160 nM. At 14 μM PCPS the initiation phase was extended to 9 min, thrombin generation rate decreased to 13 nM/min (▲; FIG. 9C) and the maximum thrombin level decreased to 70 nM. No thrombin generation was observed in the absence of PCPS (○; FIG. 9C).

PCPS and Factor VIIa in "Acquired" Hemophilia B Blood.

Figure 10A:
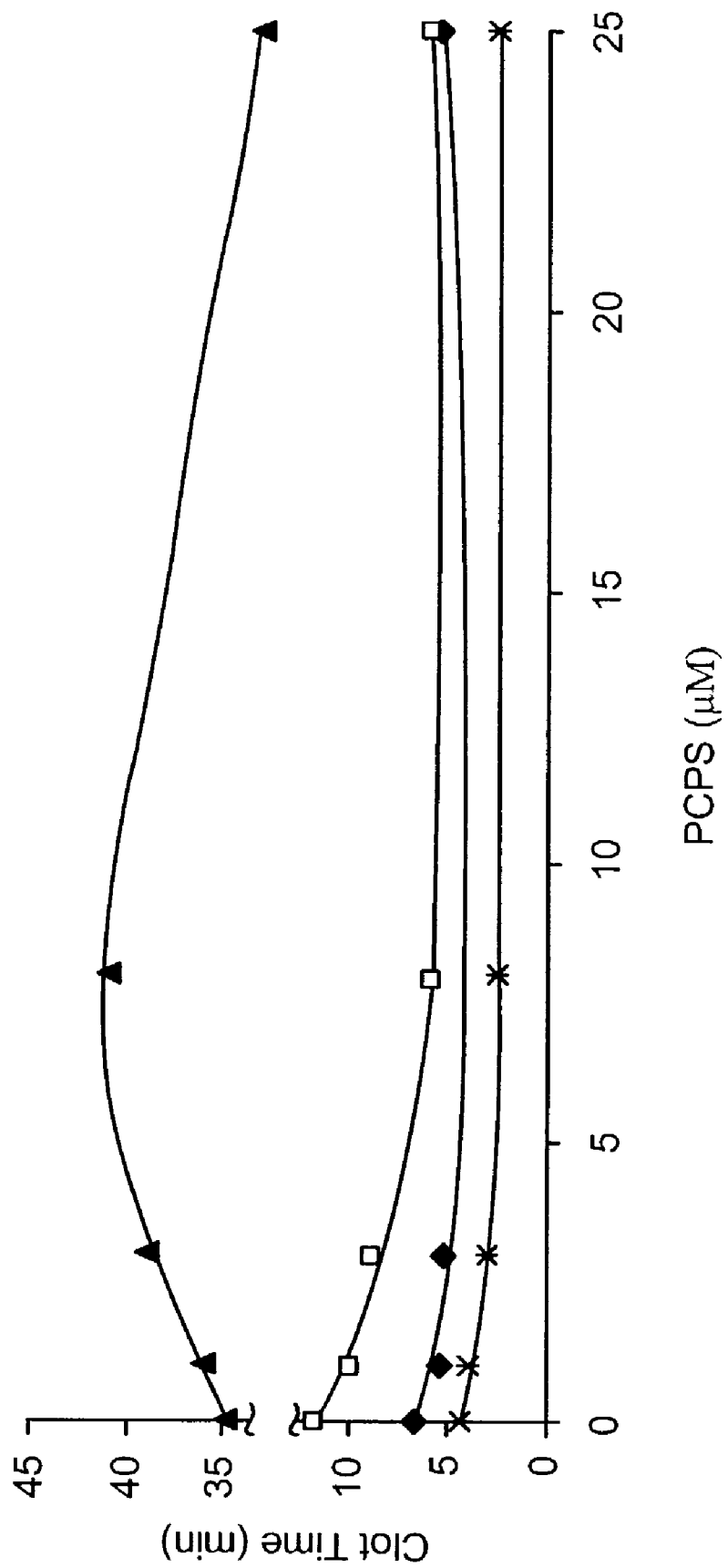
FIGS. 10A–10B are graphs showing PCPS titration in normal and "acquired" hemophilia B blood. Cloning of the CTI-inhibited (0.1 mg/ml) normal blood (♦) was induced with 5 pM relipidated TF at varying PCPS concentrations. Clotting of "acquired" hemophilia B blood was initiated either with 10 nM factor VIIa in the absence of TF (▲) or with 5 pM TF in the absence ( ) and in the presence of 10 nM factor VIIa (*).

PCPS titration: CTI-inhibited normal blood activated with 5 pM TF/25 nM PCPS clotted in 6.9 min (Table 1; FIG. 10A, ♦). The addition of 1 μM PCPS decreased the clotting time to 5.5 min. Further increases in PCPS concentration (to 25 μM) had no additional effect on the clotting time. "Acquired" hemophilia B blood in the presence of 5 pM TF/25 nM PCPS clotted in 11.8 min ( ). At 3 μM PCPS the clotting time of this blood was decreased to 10.1 min. An increase in PCPS to 8 μM decreased clotting time to 5.8 min. A further increase in PCPS to 25 μM had no additional effect on clotting time. The addition of 10 nM factor VIIa at 5 pM TF/25 nM PCPS decreased the visually observed clotting time of "acquired" hemophilia B blood from 11.8 min (without exogenous factor VIIa; FIG. 10A) to 4.3 min (* FIG. 10A). Increases in PCPS concentration, decreased the clotting time gradually to 2.5 min at 25 μM phospholipid. When TF was omitted from the reaction, the "acquired" hemophilia B blood clotted in 35 min in the presence of 10 nM factor VIIa (▲; FIG. 10A). In the absence of TF, the additions of PCPS (1–25 μM) had no procoagulant effect on the clotting time of the "acquired" hemophilia B blood (clotting time varied from 33 to 41 min).

TABLE 1

Parameters of thrombin generation in normal and "acquired" hemophilia B blood (AHBB) activated with 5 pM TF.

| | | | Thrombin generation | | | |
|---|---|---|---|---|---|---|
| | Saturating PCPS | Clot time (min) | Max. rate (nM/min) | | Max. conc. (nM) | |
| Conditions | (μM) | A | B | A | B | A | B |
| Normal blood | 3 | 6.9 | 5.5 | 60 | 135 | 500 | 700 |
| AHBB | 25 | 11.8 | 5.9 | 21 | 97 | 240 | 570 |
| AHBB + 10 nM factor VIIa | 25 | 4.3 | 2.6 | 43 | 219 | 180 | 570 |
| AHBB[#] | NA | 35 | 33[9] | 1.6 | 0.2[9] | 56 | 6.9[9] |

A - at 25 nM PCPS;
B - at saturating PCPS;
NA - not applicable;
[#]no TF added;
[9]at 25 μM PCPS The maximum thrombin concentration (evaluated as the plateau level of the TAT generation) achieved in normal blood activated with 5 pM TF/25 nM PCPS was ~500 nM (Table 1). An increase in PCPS to 3 μM increased the maximum thrombin observed to ~700 nM. Further increases in the PCPS concentration (up to 25 μM) had no additional effect on the ultimate thrombin concentration. The maximum thrombin level observed in "acquired" hemophilia B blood at the same initiator concentration (no additional PCPS) was ~240 nM. The addition of PCPS (25 μM) increased the thrombin level to 570 nM. When 10 nM factor VIIa was added to "acquired" hemophilia blood at 5 pM TF and 3 μM PCPS, an equivalent thrombin level (570 nM) was achieved. No further increase in thrombin was observed when PCPS was increased to 8 and 25 μM. In the absence of TF, the addition of 10 nM factor VIIa to "acquired" hemophilia B blood produced a maximum thrombin level of 56 nM after 45 min. In the absence of TF, the addition of PCPS (1–25 μM) with 10 nM factor VIIa to "acquired" hemophilia B blood did not increase the final thrombin concentration.

Figure 10B:
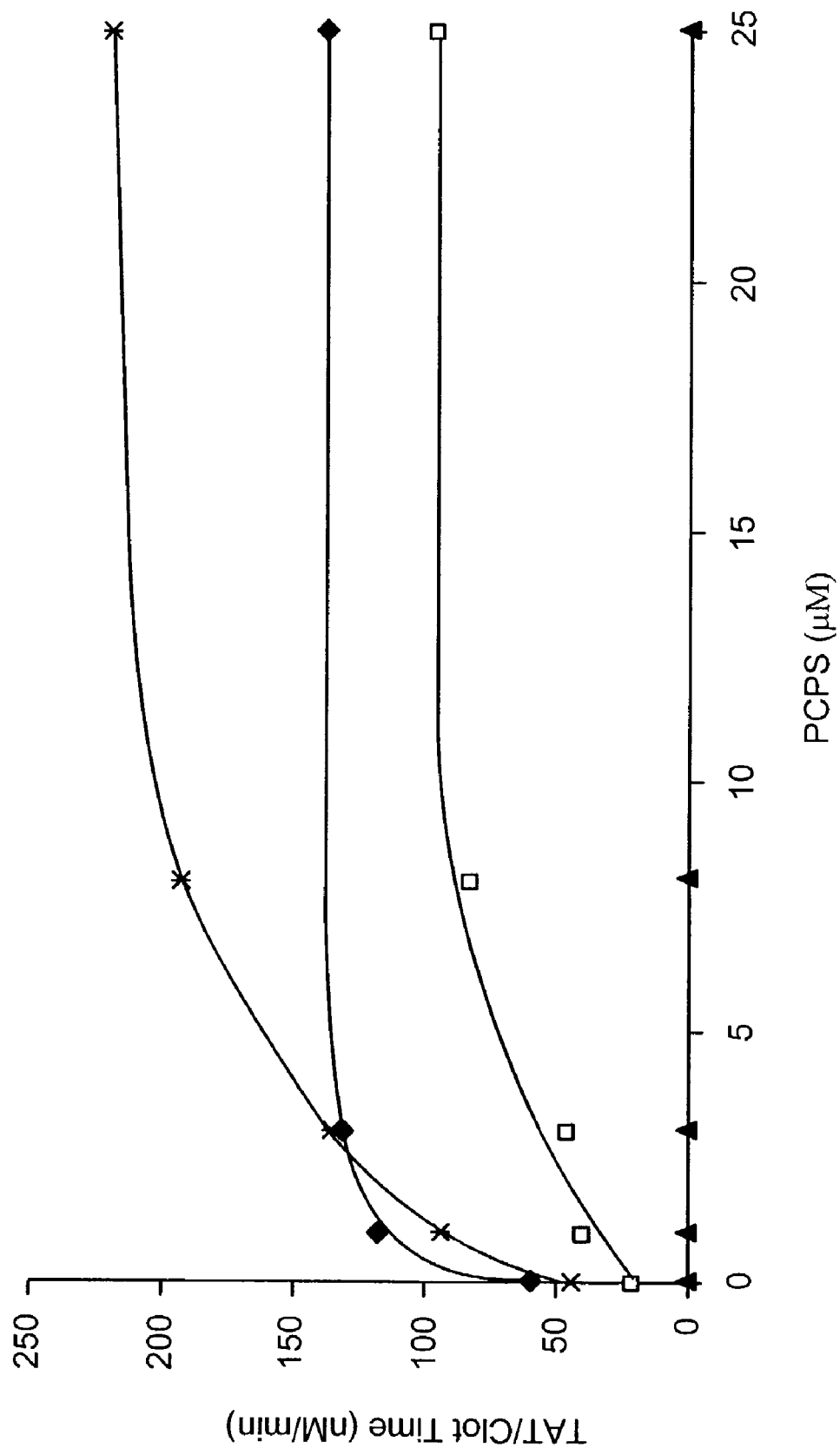

Thrombin generation rates presented in FIG. 10B were calculated dividing maximum thrombin levels generated (based on TAT formation) by the clotting time. In normal blood activated with 5 pM TF (no exogenous factor VIIa added), thrombin generation rates varied from 60 nM/min without PCPS addition to 135 nM/min at 25 μM PCPS (Table 1; FIG. 10 B; ♦). In "acquired" hemophilia B blood activated with the same TF concentration in the absence of additional PCPS, the thrombin generation rate was approximately ⅓ that of normal blood (21 nM/min) (; FIG. 10B). With increasing PCPS this rate increased, reaching 97 nM/min at 25 μM phospholipid. The addition of 10 nM factor VIIa to "acquired" hemophilia B blood induced to clot with 5 pM TF increased the thrombin generation rate at all PCPS concentrations tested (*; FIG. 10B). At 3 μM PCPS, the thrombin generation rate in "acquired hemophilia B blood with 10 nM factor VIIa was similar to that observed in normal blood at the same PCPS concentration in the absence of exogenous factor VIIa (134 and 132 nM/min, respectively). In the absence of TF and PCPS, the addition of 10 nM factor VIIa to "acquired" hemophilia B blood produced low levels of thrombin (56 nM) at a low (1.6 nM/min) rate (▲; FIG. 10B). Additions of PCPS (1–25 μM) did not increase thrombin generation rate.

These data indicate that for normal blood in the presence of TF, saturation with PCPS was achieved at 3 μM phospholipid. In "acquired" hemophilia B blood in both the absence and presence of 10 nM exogenous factor VIIa, the maximum thrombin generation rates were observed at 25 μM PCPS. In the absence of TF and in the presence of 10 nM factor VIIa, thrombin generation in "acquired" hemophilia B blood was negligible and almost independent of PCPS.

Figure 11A:
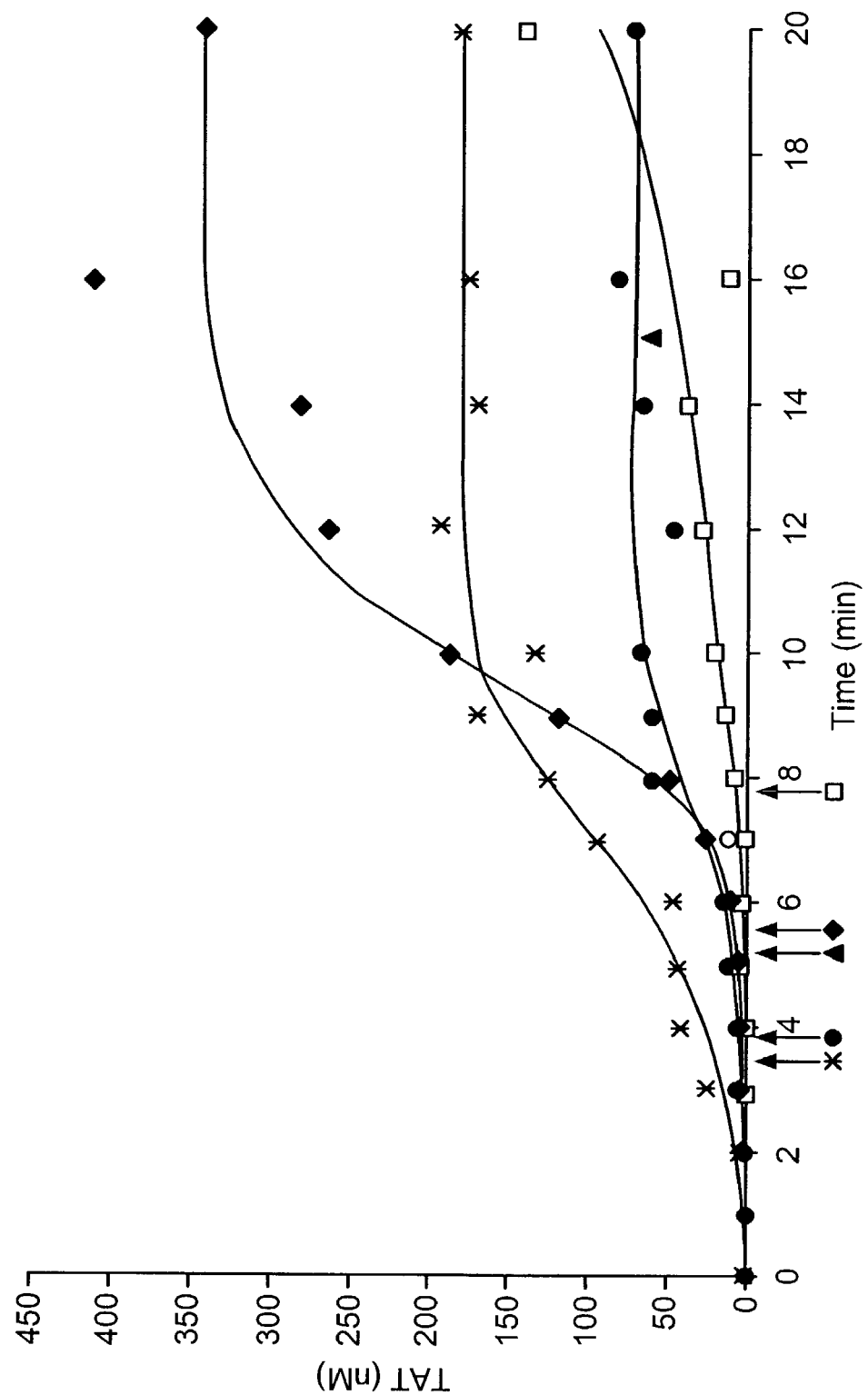
FIGS. 11A to 11C are graphs showing the TF-initiated cloning of normal and "acquired" hemophilia B blood. Cloning of the CTI-inhibited (0.1 mg/ml) normal (♦) and "acquired" hemophilia B ( ) blood was induced with 4 pM relipidated TF. 10 nM factor VIIa alone (▲), 15 µM PCPS alone (•) and both 10 nM factor VIIa and 15 µM PCPS (*) were added to "acquired" hemophilia B blood. Arrows indicate clotting times.
Figure 11B:
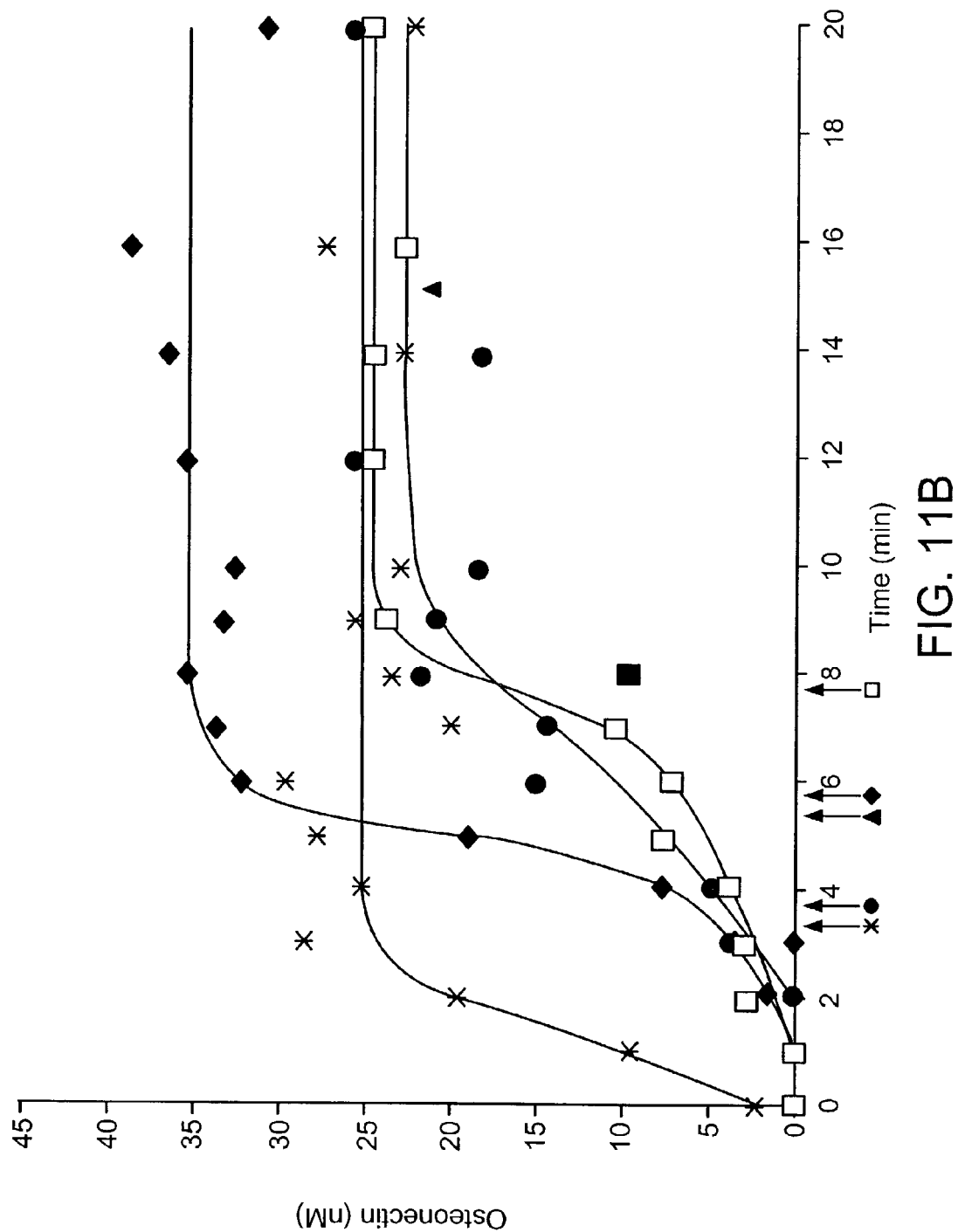

Time-course of thrombin generation and clot formation: In all experiments of this series blood was activated with 4 pM TF/20 nM PCPS. Normal CTI-inhibited blood clotted 5.5 min after the addition of TF (Table 2; FIG. 11; ♦). Thrombin generation occurred at a maximum rate of 68 nM/min and the reaction was complete ~15 min after TF addition. The clotting time of "acquired" hemophilia B blood at the same TF concentration was extended to 7.8 min ( ) with a maximum thrombin generation rate of 5.7 nM/min and the maximum level of 36 nM; values less than 10% those observed in normal blood. The addition of 15 μM PCPS to "acquired" hemophilia B blood (•; FIG. 11A) decreased the visually observed clotting time to 3.9 min, i.e. a clot was observed almost 2 min sooner than in normal blood, however, the inception of the propagation phase of thrombin generation occurred at the same time as in normal blood (6 min). The maximum rate of thrombin generation was enhanced to 48 nM/min and the maximum level increased to 70 nM. The addition of 10 nM factor VIIa to "acquired" hemophilia B blood activated with 4 pM TF in the presence of 15 μM PCPS (*) had almost no effect on the visually observed clotting time (3.7 min), i.e. it was similar to that observed in the absence of added factor VIIa. The initiation phase of thrombin generation, however, was shortened to 3 min, and maximum levels increased to 200 nM. The addition of 10 nM factor VIIa alone, without PCPS to "acquired" hemophilia B blood activated with 4 pM TF produced 60 nM thrombin over 15 min of the reaction (▲).

TABLE 2

Parameters of clot formation in normal and "acquired" hemophilia B blood (AHBB) activated with 4 pM TF.

| Conditions | Clot time (CT) min | Analyte in solution at CT % of total | | Final clot weights mg/ml blood |
|---|---|---|---|---|
| | | Fibrinogen | FPA | |
| Normal blood | 5.5 | 20 | 70 | 1.0 |
| AHBB | 7.8 | 40 | 60 | 0.7 |
| AHBB + 10 nM factor VIIa | 5.7 | NE | NE | 0.7 |
| AHBB + 15 μM PCPS | 4.0 | 65 | 50 | 0.9 |
| AHBB + 10 nM factor VIIa + 15 μM PCPS | 3.7 | 10 | 85 | 1.1 |

NE - not evaluated

Platelet activation (based upon platelet osteonectin release) in normal blood induced to clot with 4 pM TF (FIG. 11B; ♦) was detected between 1 and 2 min after the initiation of the reaction and release occurred at a rate of 1.3 nM/min, approximately 10% the maximum rate (12.9 nM/min). In "acquired" hemophilia B blood ( ), detectable platelet activation occurred after similar interval with initial rates as in normal blood. However, the maximum rate of this process (6.9 nM/min) was decreased by half and delayed, occurring between 7 and 9 min of the reaction. The addition of 15 μM PCPS to "acquired" hemophilia B blood had little effect on platelet activation (•). When both 10 nM factor VIIa and 15 μM PCPS were added to this blood, early and rapid platelet activation occurred at a rate of 9.6 nM/min (*).

Figure 11C:
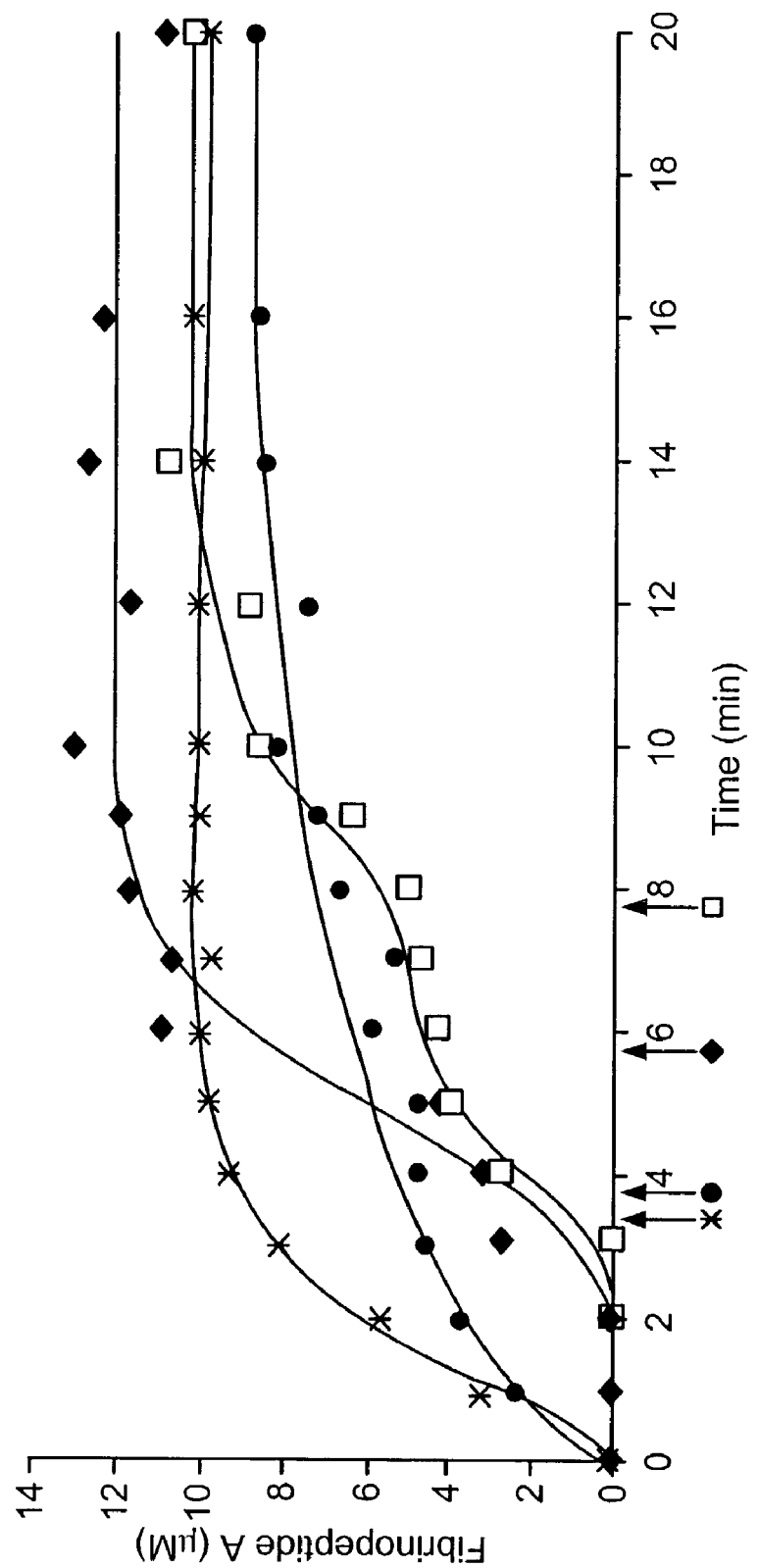

In normal blood activated with 4 pM TF, approximately 70% of total FPA was released at the clotting time at a maximum rate of 4.2 μM/min (Table 2; FIG. 11C; ♦). In "acquired" hemophilia B blood, detectable FPA release was delayed by more than 1 min and the maximum rate decreased to 1.2 μM/min ( ). Approximately 60% of this peptide were released at the clotting time. The addition of 15 μM PCPS to "acquired" hemophilia B blood, substantially shifted the inception of the FPA release to the left although maximum rate of release (1.3 μM/min) was almost not affected (•). Less than 50% of FPA were released at clotting time. When 10 nM factor VIIa together with 15 μM PCPS were added to "acquired" hemophilia B blood, the maximum rate of the FPA release was increased to 2.9 μM/min (*). At the visually observed clotting time, 85% of total available FPA was in solution.

Figures 12A, 12B, 12C, 12D:
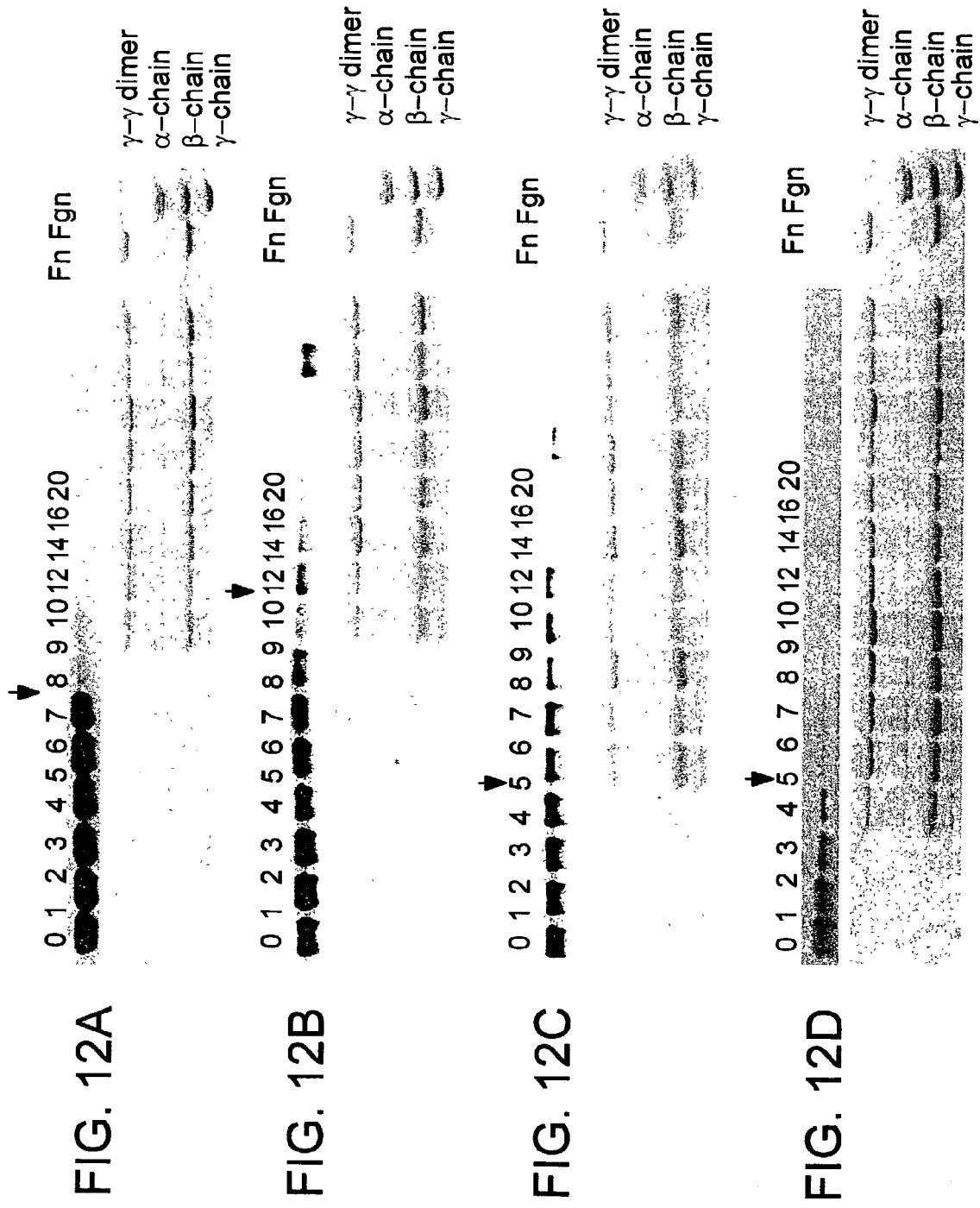
FIG. 12 is a photograph of gels showing depletion of fibrinogen (Fgn) and solid clot formation during TF-induced clotting of whole blood. Samples for analyses were taken from experiments of FIG. 11. Upper lanes in each panel represent soluble fibrinogen, lower parts represent solubilized solid clots. Panel A normal blood; panel B "acquired" hemophilia B blood; panel C "acquired" hemophilia B blood with 15 µM PCPS; panel D "acquired" hemophilia B with 15 µM PCPS and 10 nM factor VIIa. Arrows indicate clotting times.

Soluble fibrinogen depletion and insoluble clot formation in normal and induced hemophilia B blood are presented in FIG. 12 and Table 2. In normal blood induced to clot with 4 pM TF (FIG. 12, panel A), soluble fibrinogen was almost completely removed from the solution at the visually observed clotting time. In "acquired" hemophilia B blood, fibrinogen depletion and solid clot formation were delayed and approximately 40% of total fibrinogen was in solution at the clotting time (FIG. 12, panel B). Only 35% of total fibrinogen was depleted from the solution at the clotting time when 15 μM PCPS were added to "acquired" hemophilia B blood (FIG. 12, panel C). When both 10 nM factor VIIa and 15 μM PCPS were added to "acquired" hemophilia B blood (FIG. 12, panel D), the onset of the fibrinogen depletion started substantially earlier than in normal blood (compare FIG. 12, panels A and D). Only 10% of fibrinogen was in solution at the visually observed clotting time.

Figure 13:
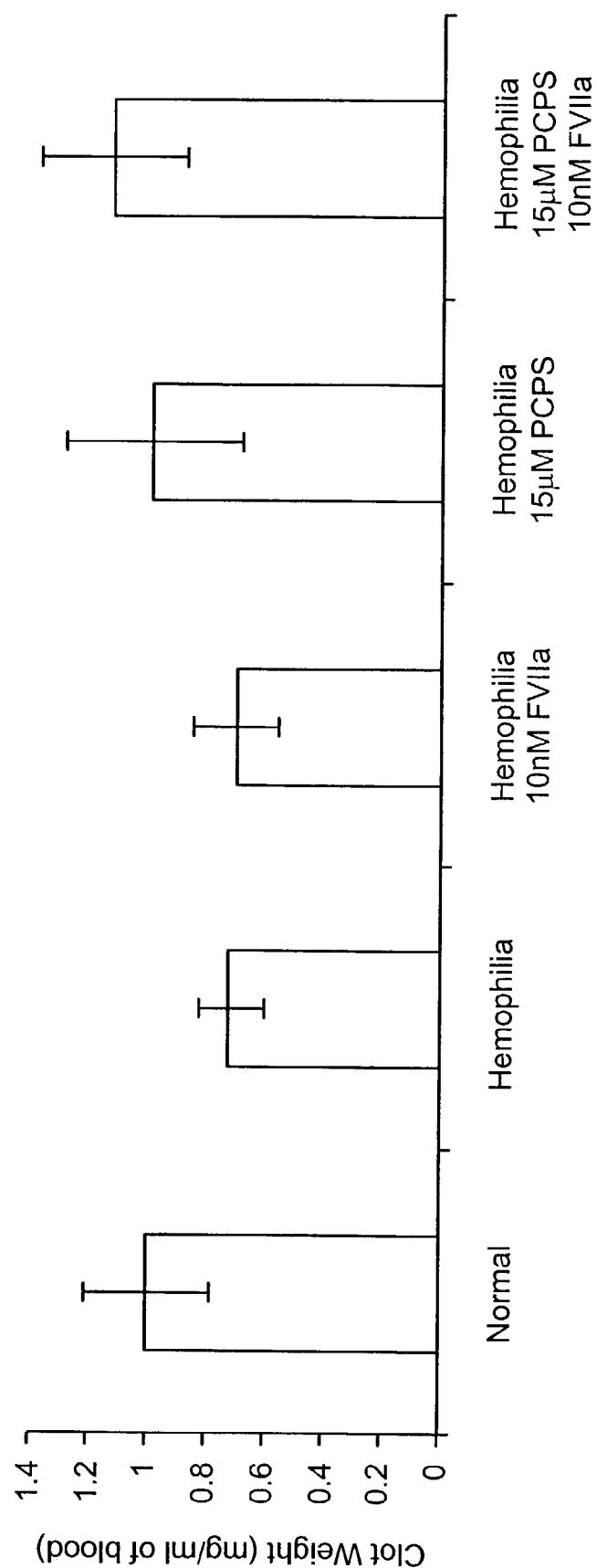
FIG. 13 is a bar graph showing the clot weights in TF-induced normal and "acquired" hemophilia B blood. Clots were taken from experiments of FIG. 11.

The final clot weights in normal blood were 1.0 mg/ml of blood (Table 2; FIG. 13). In "acquired" hemophilia B blood, final clot weights were decreased to 0.7 mg and not affected by the addition of 10 nM factor VIIa. When 15 μM PCPS was added to "acquired" hemophilia B blood, final clot weights increased to an average of 0.9 mg, whereas addition of both 10 nM factor VIIa and 15 μM PCPS increased clot weights to 1.1 mg.

The dynamics of clot growth over time revealed a pronounced dependence upon the conditions of the reaction. In normal blood, initial clot weights were ~60% of those final (on average 0.6 vs. 1.0 mg). In "acquired" hemophilia B blood, initial weights were ~50% of final (0.33 vs. 0.7 mg). In "acquired" hemophilia B blood with 15 μM PCPS, although clots were formed relatively early (4 min after the initiation), they were initially small (0.1–0.3 mg) and stayed such for ~5 min. In the presence of 10 nM exogenous factor VIIa and 15 μM PCPS in "acquired" hemophilia B blood, clots of a normal weight (0.9–1.2 mg) were formed early in the reaction (3 min after TF addition).

The data indicate that anionic phospholipids remarkably improve the hemostatic potential of factor VIIa in the tissue factor-induced coagulation of "acquired" hemophilia B blood in vitro. In the presence of factor VIIa at a pharmacological concentration (10 nM) and phospholipids at 8 μM, all parameters of thrombin generation and clot formation in "acquired" hemophilia B blood are similar to those observed in normal blood. Factor VIIa and PCPS alone are able to correct the visually observed clotting time. In the absence of TF, only negligible amounts of thrombin are generated at a low rate when 10 nM factor VIIa is added to the hemophilia B blood, and they are not increased by the addition of phospholipids. These data are consistent with our previous conclusion that TF is essential to achieve normal hemostasis in hemophilia blood in the presence of factor VIIa at pharmacological concentrations (See Butenas S, Brummel K E, Branda R F, Paradis S G, Mann K G. "Mechanism of Factor VIIa-Dependent Coagulation in Hemophilia Blood." Blood. 2002;99:923–930).

Our results also show thrombin generation profiles are observed for the reactions accomplished either in the presence of platelets present at physiological concentrations or in the presence of 1–2 μM phospholipids (See Butenas S, Branda R F, van't Veer C, Cawthern K M, Mann K G. "Platelets and Phospholipids in Tissue Factor-InitiatedTthrombin Generation." Thromb Haemost. 2001 ;86:660–667). These concentrations of phospholipids, however, are much lower than those required to saturate the complex enzymes of blood coagulation. An addition of phospholipids to blood provides an extra surface for the reactions of blood coagulation to occur and, as a consequence, increases the potency of enzymatic complexes of blood coagulation. The proteolytic activity of the factor VIIa/TF complex is substantially affected due to the high saturating concentrations of phospholipids (>100 μM) required for the maximum efficiency of this enzymatic complex (See Butenas S, Branda R F, van't Veer C, Cawthern K M, Mann K G. "Platelets and Phospholipids in Tissue Factor-InitiatedTthrombin Generation." Thromb Haemost. 2001 ;86:660–667).

At phospholipid addition, factor VIIa/TF is able to generate factor Xa at a high rate. An addition of 10 nM factor VIIa to blood saturates TF present and, as a consequence, increases concentration of the factor VIIa/TF complex. However, neither phospholipids alone nor factor VIIa alone are able to increase factor Xa concentration to the levels required for an efficient propagation phase of thrombin generation to occur. Only a combined effect of both increased concentration and increased efficiency of the factor VIIa/TF complex produces factor Xa levels substantial enough to drive thrombin generation over the threshold.

In summary, phospholipids substantially improve the hemostatic potential of factor VIIa in the tissue factor induced coagulation of "acquired" hemophilia B blood. The in vivo efficacy of factor VIIa replacement therapy probably requires a simultaneous presence of TF and excess membrane phospholipids. This can lead to decreased both amounts of factor VIIa and duration of treatment required to achieve normal hemostasis in hemophilia blood.

All references disclosed herein are incorporated by reference.

REFERENCES

1. Higgins D L, Mann K G. The interaction of bovine factor V and factor V-derived peptides with phospholipid vesicles. *J. Biol Chem.* 1983;258:6503–6508.
2. Brummel K E, Butenas S, Mann K G. An integrated study of fibrinogen during blood coagulation. *J. Biol Chem.* 1999;274:22862–22870.
3. Bajaj S P, Rapaport S I, Prodanos C. A simplified procedure for purification of human prothrombin, factor IX and factor X. *Prep Biochem.* 1981 ;11:397–412.
4. van't Veer C, Mann K G. Regulation of tissue factor initiated thrombin generation by the stoichiometric inhibitors tissue factor pathway inhibitor,. antithrombin-III, and heparin cofactor-II. *J. Biol Chem.* 1997;272:4367–4377.
5. Katzmann J A, Nesheim M E, Hibbard L S, Mann K G. Isolation of functional human coagulation factor V by using a hybridoma antibody. *Proc Nat'l Acad Sci USA.* 1981;78:162–166.
6. Griffith M J, Noyes C M, Church F C. Reactive site peptide structural similarity between heparin cofactor II and antithrombin III. *J. Biol Chem.* 1985;260:2218–2225.
7. Cawthern K M, van't Veer C, Lock J B, DiLorenzo M, Branda R F, Mann K G. Blood coagulation in hemophilia A and hemophilia C. *Blood.* 1998;91:4581–4592.
8. Mustard J F, Perry D W, Ardlie N G, Packham M A. Preparation of suspension of washed platelets from humans. *Br J Hematol.* 1972;22:193–204.
9. Wilcox J N, Smith K M, Schwartz S M, Gordon D. *Proc. Nat'l. Acad. Sci. USA,* 1989;86:2839–2843.
10. Weiss H J, Turitto V T, Maumgartner H R, Nemerson Y, Hoffmann T. *Blood,* 1989;73:968–975.
11. Carlsen E, Flatmark A, Prydz H. *Transplantation,* 1988; 46:575–580.
12. Bevilaqua M P, Pober J S, Majeau G R et al. *Proc. Nat'l. Acad. Sci. USA,* 1986;83:4533–4537.
13. Yang H L, Lu F J, Wung S L et al. *Thromb. Haemost.,* 1994;71:325–330.
14. Camera M, Giesen P L, Fallon J et al. *Arterioscler. Thromb. Vasc. Biol.,* 1999;19:531–537.
15. Lawson J H, Krishnaswamy S, Butenas S, Mann K G. Extrinsic pathway proteolytic activity. *Methods Enzymol.* 1993;222:177–195.
16. Rand M D, Lock J B, van't Veer C, Gaffney D P, Mann K G. Blood clotting in minimally altered whole blood. *Blood.* 1996;88:3432–3445.
17. Lawson J H, Kalafatis M, Stram S, Mann K G. A model for the tissue factor pathway to thrombin. I. An empirical study. *J. Biol Chem.* 1994;269:23357–23366.
18. Santagostino E, Morfini M, Rocino A, Baudo F, Scaraggi F A, Gringeri A. Relationship between recombinant factor VIIa activity and clinical efficacy of recombinant factor VIIa given by continuous infusion to patients with factor VIII inhibitors. *Thromb Haemost.* 2001;86:954–958.

What is claimed is:

1. A pharmaceutically acceptable composition for controlling bleeding in a human, the composition comprising from about 0.1 nM to about 10 nM recombinant Factor VIIa, and phospholipid vesicles, the phospholipid vesicles comprising phosphatidylcholine and phosphatidylserine (PCPS), wherein the PCPS comprise from about 50% (w/v) to about 90% (w/v) phosphatidylcholine and from about 10% (w/v) to about 50% (w/v) phosphatidylserine.

2. A pharmaceutically acceptable composition for controlling bleeding in a human, the composition comprising from about 0.1 nM to about 10 nM recombinant Factor VIIa, and phospholipid vesicles, the phospholipid vesicles comprising phosphatidylcholine and phosphatidylserine (PCPS), wherein the PCPS comprise from about 50% (w/v) to about 90% (w/v) phosphatidylcholine and from about 10% (w/v) to about 50% (w/v) phosphatidylserine;
   wherein the weight ratio of the PCPS to the recombinant Factor VIIa is from about 0.15:1 to about 30,000:1.

3. A pharmaceutically acceptable composition for controlling bleeding in a human, the composition comprising a coagulation-effective amount of a substantially pure human blood coagulation Factor VIIa and phospholipid vesicles, wherein the blood coagulation factor does not form a binding complex with Factor Va to produce thrombin;
   wherein the coagulation-effective amount of blood coagulation Factor VIIa is from about 10 to 1000 fold less than a therapeutic amount;
   wherein the phospholipid vesicles comprise anionic phospholipids at about physiological pH;
   wherein the anionic phospholipids are phosphatidylcholine and phosphatidylserine (PCPS);
   wherein the Factor VIIa is recombinant; and
   wherein the composition comprises Factor VIIa in an amount from about 0.1 nM to about 10 nM (from about 18 units/kg to about 1,800 units/kg).

4. A pharmaceutically acceptable composition for controlling bleeding in a human, the composition comprising a coagulation-effective amount of a substantially pure human blood coagulation Factor VIIa and phospholipid vesicles, wherein the blood coagulation factor does not form a binding complex with Factor Va to produce thrombin;
   wherein the coagulation-effective amount of blood coagulation factor VIIa is from about 10 to 1000 fold less than a therapeutic amount;
   wherein the phospholipid vesicles comprise anionic phospholipids at about physiological pH;
   wherein the anionic phospholipids are phosphatidylcholine and phosphatidylserine (PCPS);
   wherein the Factor VIIa is recombinant;
   wherein the composition comprises Factor VIIa in an amount from about 0.1 nM to about 10 nM (from about 18 units/kg to about 1,800 units/kg); and
   wherein the phospholipid vesicles are phosphatidylcholine and phosphatidylserine (PCPS), the PCPS comprising from about 50% (w/v) to about 90% (w/v) phosphatidylcholine and from about 10% (w/v) to about 50% (w/v) phosphatidylserine.

5. A pharmaceutically acceptable composition for controlling bleeding in a human, the composition comprising a coagulation-effective amount of a substantially pure human blood coagulation Factor VIIa and phospholipid vesicles, wherein the blood coagulation factor does not form a binding complex with Factor Va to produce thrombin;
   wherein the coagulation-effective amount of blood coagulation factor VIIa is from about 10 to 1000 fold less than a therapeutic amount;

wherein the phospholipid vesicles comprise anionic phospholipids at about physiological pH;
wherein the anionic phospholipids are phosphatidylcholine and phosphatidylserine (PCPS);
wherein the Factor VIIa is recombinant;
wherein the composition comprises Factor VIIa in an amount from about 0.1 nM to about 10 nM (from about 18 units/kg to about 1,800 units/kg);
wherein the phospholipid vesicles are phosphatidylcholine and phosphatidylserine (PCPS), the PCPS comprising from about 50% (w/v) to about 90% (w/v) phosphatidylcholine and from about 10% (w/v) to about 50% (w/v) phosphatidylserine; and
wherein the PCPS is present in an amount from about 1 arbitrary unit to about 3,000 arbitrary units per kg body weight of the human.

6. A pharmaceutically acceptable composition for controlling bleeding in a human, the composition comprising a coagulation-effective amount of a substantially pure human blood coagulation factor VIIa and phospholipids vesicles, wherein the blood coagulation factor does not form a binding complex with Factor Va to produce thrombin;
wherein the coagulation-effective amount of blood coagulation Factor VIIa is from about 10 to 1000 fold less than a therapeutic amount;
wherein the phospholipids vesicles comprise anionic phospholipids at about physiological pH;
wherein the anionic phospholipids are phosphatidylcholine and phosphatidylserine (PCPS);
wherein the Factor VIIa is recombinant;
wherein the composition comprises Factor VIIa in an amount from about 0.1 nM to about 10 nM (from about 18 units/kg to about 1,800 units/kg);
wherein the phospholipid vesicles are phosphatidylcholine and phosphatidylserine (PCPS), the PCPS comprising from about 50% (w/v) to about 90% (w/v) phosphatidylcholine and from about 10% (w/v) to about 50% (w/v) phosphatidylserine;
wherein the PCPS is present in an amount from about 1 arbitrary unit to about 3,000 arbitrary units per kg body weight of the human; and
wherein the weight ratio of the PCPS to the recombinant Factor VIIa is from about 0.15:1 to about 30,000:1.

7. A method for controlling bleeding in a human, wherein the method comprises administering to the human a pharmaceutically acceptable composition comprising a coagulation-effective amount of blood coagulation Factor VIIa and phospholipid vesicles, wherein the coagulation factor does not form a specific binding complex with Factor Va; and controlling the bleeding in the human.

8. The method of claim 7, wherein the coagulation-effective amount is from about 10 to 1000 fold less than a therapeutic amount of the blood coagulation factor VIIa required to control bleeding in a human in the absence of phospholipids.

9. The method of claim 8, wherein the Factor VIIa is recombinant.

10. The method of claim 9, wherein the composition comprises Factor VIIa in an amount from about 0.1 nM to about 10 nM.

11. The method of claim 10, wherein the phospholipid vesicles are phosphatidylcholine and phosphatidylserine (PCPS), the PCPS comprising from about 50% (w/v) to about 90% (w/v) phosphatidylcholine and from about 10% (w/v) to about 50% (w/v) phosphatidylserine.

12. The method of claim 11, wherein the PCPS is present in an amount from about 1 arbitrary unit to about 3,000 arbitrary units per kg body weight of the human.

13. The method of claim 12, wherein the amount of recombinant Factor VIIa is from about 18 units to about less than 1,800 units per kg of body weight of the human.

14. The method of claim 13, wherein the weight ratio of the PCPS to the Factor VIIa is from 0.15:1 to 30,000: 1.

15. The method of claim 7, wherein the phospholipid vesicles comprise anionic phospholipids at about physiological pH.

16. The method of claim 15, wherein the anionic phospholipids are phosphatidylcholine and phosphatidylserine (PCPS).

17. A method for controlling bleeding in a human, the method comprising administering to the human a pharmaceutically acceptable composition comprising a recombinant Factor VIIa in an amount from about 0.1 nM to about 10 nM and phospholipid vesicles, the phospholipid vesicles comprising phosphatidylcholine and phosphatidylserine (PCPS), wherein the PCPS comprise from about 50% (w/v) to about 90% (w/v) phosphatidylcholine and from about 10% (w/v) to about 50% (w/v) phosphatidylserine.

18. The method of claim 17, wherein the PCPS is present in an amount from about 1 arbitrary unit to about 3,000 arbitrary units per kg body weight of the human.

19. The method of claim 18, wherein the amount of recombinant Factor VIIa is from about 18 units to about less than 1,800 units per kg of body weight of the human.

20. The method of claim 17, wherein the weight ratio of the PCPS to the Factor VIIa is from 0.15:1 to 30,000:1.

21. A method for reducing a therapeutic amount of Factor VIIa required to control bleeding in a human comprising contacting Factor VIIa with phospholipid vesicles in a solution and administering the Factor VIIa/phospholipid solution to a human, wherein the amount of Factor VIIa administered is less than the therapeutic amount of Factor VIIa required to control bleeding in a human in the absence of phospholipids, and wherein the bleeding is controlled by the administration of the Factor VIIa/phospholipid vesicle solution.

22. The method of claim 21, wherein the amount of blood coagulation factor administered to the patient is from about 10 to 1000 fold less than the therapeutic amount.

23. The method of claim 22, wherein the amount of recombinant Factor VIIa administered is from about 0.1 nM to about 10 nM.

24. The method of claim 21, wherein the human patient is suffering from or suspected of suffering from disorder associated with an inadequate level of at least one blood coagulation factor.

25. The method of claim 24, wherein the disorder is hemophilia.

* * * * *